United States Patent
Ando et al.

(10) Patent No.: US 7,163,609 B2
(45) Date of Patent: Jan. 16, 2007

(54) GAS SENSOR HAVING A LAMINATE COMPRISING SOLID ELECTROLYTE LAYERS AND ALUMINA SUBSTRATE

(75) Inventors: Masashi Ando, Aichi (JP); Takao Kojima, Aichi (JP); Shigeki Mori, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 544 days.

(21) Appl. No.: 10/338,740

(22) Filed: Jan. 9, 2003

(65) Prior Publication Data

US 2004/0084309 A1    May 6, 2004

(30) Foreign Application Priority Data

Nov. 1, 2002   (JP)   ............................. 2002-320479

(51) Int. Cl.
G01N 27/409    (2006.01)
G01N 27/41     (2006.01)

(52) U.S. Cl. .................. 204/425; 204/426; 204/428

(58) Field of Classification Search ............... 204/425, 204/426, 427, 428; 205/783.5; 73/23.31, 73/23.32
See application file for complete search history.

(56) References Cited

U.S. PATENT DOCUMENTS

| | | | |
|---|---|---|---|
| 4,334,974 A * | 6/1982 | Muller et al. ................. | 204/425 |
| 4,360,598 A * | 11/1982 | Otagiri et al. ............... | 501/103 |
| 4,733,056 A | 3/1988 | Kojima et al. | |
| 4,755,274 A | 7/1988 | Mase et al. | |
| 4,765,880 A | 8/1988 | Hayakawa et al. | |

(Continued)

FOREIGN PATENT DOCUMENTS

EP    0 414 575 A1    2/1991

(Continued)

OTHER PUBLICATIONS

British Search Report for British Patent Application No. GB 0300497.5 dated Jun. 13, 2003.

*Primary Examiner*—Kaj K. Olsen
(74) *Attorney, Agent, or Firm*—Sughrue Mion, PLLC

(57) ABSTRACT

A gas sensor (1a) having a laminate including an alumina substrate (11) having a heating resister (115) embedded in the alumina substrate (11); a first oxygen-ion conductive solid electrolyte layer (131) containing zirconia and alumina and partly constituting an oxygen-detecting cell (13) and the first solid electrolyte layer (131) being laminated with said alumina substrate (11); a second oxygen-ion conductive solid electrolyte layer (121) containing zirconia and alumina and partly constituting an oxygen-pumping cell (12); an ion-leakage preventing ceramic spacer (143) for preventing oxygen-ions from leaking from the second oxygen-ion conductive solid electrolyte layer (121) to the first oxygen-ion conductive solid electrolyte layer (131), the spacer (143) being laminated between the first and second oxygen-ion conductive solid electrolyte layers (131, 121); and a gas-diffusion space (141) formed between an electrode (133) of the oxygen-detecting cell (13) and an electrodes (126) of the oxygen-pumping cell (12). Furthermore, the laminate (1a) is co-fired. Preferably, the zirconia contained at least in the second solid electrolyte layer is made of partially stabilized zirconia, the phase formed in the zirconia consisting essentially of tetragonal and cubic phases. Additionally, an ionic migration-preventing electrode (117) is optionally embedded in the alumina substrate (11) for preventing metal ion migration.

49 Claims, 4 Drawing Sheets

U.S. PATENT DOCUMENTS

| | | |
|---|---|---|
| 5,174,885 A | 12/1992 | Hayakawa et al. |
| 5,787,866 A * | 8/1998 | Sugiyama et al. ........... 123/672 |
| 5,895,591 A * | 4/1999 | Kojima et al. .............. 219/209 |
| 6,071,393 A * | 6/2000 | Oshima et al. ............. 204/425 |
| 2001/0047937 A1 | 12/2001 | Sugiyama et al. |

FOREIGN PATENT DOCUMENTS

| | | |
|---|---|---|
| EP | 0 548 948 A1 | 6/1993 |
| EP | 1026502 A2 | 8/2000 |
| JP | 62-44971 | 2/1987 |
| JP | 62-148849 | 7/1987 |
| JP | 3-128451 | 5/1991 |
| JP | 8-315967 | 11/1996 |
| JP | 10-221295 | 8/1998 |
| JP | 11-14594 | 1/1999 |
| JP | 2000-230919 | 8/2000 |
| JP | 2000-292406 | 10/2000 |
| JP | 2001-66280 | 3/2001 |
| JP | 2001-343354 | 12/2001 |
| JP | 2002-257784 | 9/2002 |

* cited by examiner

GAS SENSOR HAVING A LAMINATE COMPRISING SOLID ELECTROLYTE LAYERS AND ALUMINA SUBSTRATE

BACKGROUND OF THE INVENTION

1. Field of the Invention

The present invention generally relates to a gas sensor having a laminate or multilayer structure comprising at least two solid electrolyte layers and an alumina substrate, for use in an internal combustion engine, particularly to a full-range air-fuel ratio sensor (or rather a universal exhaust gas oxygen sensor) capable of measuring air-fuel ratio of an internal combustion over the entire range thereof, a nitrogen oxide gas sensor, a flammable gas sensor capable of measuring carbon monoxide or hydrocarbon, a compound gas sensor capable of measuring plural gases selected from oxygen, nitrogen oxides, carbon monoxide, hydrocarbon gas and other gases.

Specifically, the present invention relates to a gas sensor having a co-fired laminate of at least two zirconia solid electrolyte layers for electrochemical cells and an alumina substrate for embedding a heating resistor, for use, for instance, as a full-range air-fuel ratio sensor for controlling an air-fuel ratio from fuel-lean to rich in an internal combustion engine control, etc.

2. Description of the Related Art

Increasingly strict regulations have been imposed on the emission quantity of harmful matter (e.g., hydrocarbon gas, carbon monoxide, and nitrogen oxides) contained in exhaust gas discharged from an internal combustion engine of an automobile, etc. Moreover, in view of the greenhouse effect and other problems, the necessity to reduce the emission of carbon dioxide has arisen, thereby raising an urgent need for a method of further reducing consumption of fuel by internal combustion engines.

Under such circumstances, more strict requirements have been imposed on gas sensors, which are indispensable for decreasing harmful matter contained in exhaust gas and improving fuel efficiency of the internal combustion engines. In particular, in recent years, demand has arisen for a gas sensor that can activate quickly and can save electric power, while providing improved performance and reliability as well as reduction in size and cost.

U.S. Pat. No. 4,765,880 discloses a configuration of a two-cell gas sensor, including an oxygen-pumping cell and an oxygen-detecting cell. This type of two-cell gas sensor enables full-range measurement of air-fuel ratio of an internal combustion engine of an automobile, to thereby improve fuel efficiency of the internal combustion engine.

USPAP 2001/0047937 A1 discloses a multilayered air-fuel ratio sensor including solid electrolyte substrate layers and at least one heterogeneous boundary layer for absorbing thermal shock or stress interposed between the solid electrolyte substrate layers.

EP 1026502A2 discloses a one-cell type gas sensor including an alumina substrate laminated integrally with an oxygen-ion conductive solid electrolyte layer containing alumina. U.S. Pat. No. 4,733,056 discloses a technique for preventing ion-migration in a ceramic heater per se.

3. Problems Solved by the Invention

In the case of a plural cell-type sensor such as a full range air-fuel ratio sensor that requires an oxygen-pumping cell, an oxygen-concentration detecting cell, a heater for heating the cells and a cavity or space into which oxygen is pumped in or out by the pumping cell, various problems relating to activation of the sensor cells by the heater under a limited electric power consumption, an oxygen-pumping capability of the oxygen-pumping cell, measurement accuracy of the oxygen-detecting cell, reliability of the sensor, etc., arises. This is because the structure and function of the plural cell-type sensor are extremely complicated, compared to a single cell-type sensor.

In addition, electrochemical and structural weakness caused by metal-ion migration, oxygen-ion leakage between the cells, reduction or rather deoxidization of a solid electrolyte layer that constitutes the oxygen-pumping cell, etc., will be problematic in this plural-cell type sensor.

Further, when the gas sensor is designed to adopt a laminate (or multilayer structure) comprising plural zirconia oxygen-ion conductive ceramic layers and an alumina ceramic substrate (for a heating resistor to be embedded therein), etc., a serious problem such as cracks induced in the laminated zirconia ceramic layers arises due to thermal expansion difference between the zirconia ceramic layers and the alumina substrate.

A conventional two-cell type sensor used in an actual automobile combustion engine control system has been composed of two portions (namely, zirconia-sensor cells and a heater-embedded alumina substrate) bonded by a comparatively thick glass of about 200 micrometers which absorbs stress caused by the thermal expansion difference therebetween. This means at least two firing processes (one for the zirconia cells and the other for the heater-embedded alumina substrate) are necessary, resulting in a costly sensor with a slow activation of the sensor cells due to use of glass having lower thermal conductivity, as compared to alumina. Another conventional two-cell type sensor has been composed of zirconia-sensor cells and a heater-embedded zirconia substrate, which also has a disadvantage in the activation of the sensor cells due to use of the heater-embedded zirconia substrate that has insufficiently low thermal conductivity, as compared to the alumina substrate.

From a view point of activation of the sensor cells, the heater has been conventionally attached closer to the oxygen-pumping cell than to the oxygen-detecting cell. In this manner, the temperature of the oxygen-pumping cell can be elevated faster than that of the oxygen-detecting cell. This is because the cavity of the two-cell type sensor delays activation of the sensor, as compared to a single cell type sensor. If electric power for heating the heater is increased for quick activation of the sensor cells, durability and endurance of the heater is sacrificed. If the size of the sensor is made too small, the pumping capability of the oxygen-pumping cell becomes insufficient for accurate determination of the air-fuel ratio of the internal combustion engine. Because of these disadvantages, prior investigators have not been widely successful in providing or incorporating a two-cell type gas sensor into an automobile internal combustion engine and/or an exhaust gas control system thereof.

SUMMARY OF THE INVENTION

The present invention can solve the above-described problems and potential problems of the prior art, and an object of the invention is to provide a two-cell type gas sensor of having a laminate, which sensor is advantageous in terms of size, structural strength, sensor activation, electric power consumption, reliability, measurement accuracy, electrochemical endurance, durability and/or manufacturing cost.

Another object of the invention is to provide a ceramic gas sensor comprising a laminate of at least two oxygen-ion conductive ceramic layers and an alumina substrate embedding a heating resistor therein, which sensor performs quick activation, stable and accurate measurement, and structural endurance against electrochemical degradation under a severe thermal cycling condition.

Yet another object of the invention is to provide a gas sensor having a co-fired laminate of at least two oxygen-ion conductive ceramic layers for sensor cells and an alumina substrate embedding a heating resistor, which sensor has high structural strength and electrical reliability and does not malfunction due to ionic migration in the alumina substrate and deoxidization of electrodes of the cells.

The above objects of the present invention have been achieved by providing two kinds of gas sensors comprising a laminate of at least two solid electrolyte layers and an allumina substrate; one kind with an ionic migration-preventing electrode and the other without such an ionic migration-preventing electrode.

A gas sensor comprising a laminate, according to the present invention, has at least two of the following features (A) to (T) followed by at least one advantage or advantageous reason as described below. Reference numerals inserted herein or hereafter are only for the purpose of explaining the invention and do not limit the invention to specific drawings.

(A): An alumina substrate 11 is laminated onto an oxygen-detecting cell 13 and has a heating resister 115 embedded in the alumina substrate 11. Notably, as described in detail below, when an ionic migration-preventing electrode 117 is incorporated or embedded in the alumina substrate 11, the content of alumina in the alumina substrate 11 may be varied, for instance, from about 70 to 100% by weight. When the ionic migration-preventing electrode 117 is not present, the content of alumina in the alumina substrate 11 should be more than 99% by weight of alumina, preferably more than 99.9% by weight, or most preferably more than 99.99%.

An advantage of feature (A) is that good thermal transfer from the heating resistor 115 to an oxygen-pumping cell 12 through an insulating layer 111 of the alumina substrate 11 and through an oxygen-detecting cell 13 is attained and quick activation of the sensor cells 12, 13 is accomplished. This is because alumina has a higher thermal conductivity than other insulating oxide material and the alumina substrate 11 is co-fired with first and second oxygen-ion conductive solid electrolyte layers 131, 121 as described below.

(B): The first and second oxygen-ion conductive solid electrolyte layers 131, 121, partly constituting an oxygen-detecting cell 13 and an oxygen-pumping cell 12, respectively, contain zirconia and alumina so as to be laminated and co-fired with the alumina substrate 11.

An advantage of feature (B) is that alumna grains, when they are contained with zirconia in the solid electrolyte layers 131, 132, work not only as a grain-growth inhibitor for zirconia grains that are partially stabilized by a stabilizer such as yttria during sintering, but also as a phase-transformation suppressor for zirconia phase after sintering. When the average grain size of the alumina and that of the partially stabilized zirconia contained in the second oxygen-ion conductive solid electrolyte layer 121 of the oxygen-pumping cell 12 are controlled, as explained below, to be less than 1 micrometer and 2.5 micrometers respectively after sintering, the phase transformation of zirconia phase causing structural weakness of the laminate (1*a*) is effectively suppressed. Notably, the thermal expansion coefficient of alumina is about $7.7$–$8.1 \times 10^{-6}$/K and that of partially or wholly stabilized zirconia consisting substantially of tetragonal and/or cubic phase is about $9$–$12.6 \times 10^{-6}$/K, in a temperature range of 298–1150° K.

Another advantage of feature (B) is that quick activation of the pumping cell 12 is improved by including alumina in the cell electrolyte layers 121, 131. This is because the thermal conductivity of alumina is outstandingly high as compared to zirconia. The thermal conductivity of alumina is more than 10 times higher than that of zirconia at 100 degrees centigrade (Celsius).

(C): An ion-leakage preventing ceramic spacer 143 for preventing oxygen-ions from leaking from the second oxygen-ion conductive solid electrolyte layer 121 to the first oxygen-ion conductive solid electrolyte layer 131 is interposingly co-fired between the first and second oxygen-ion conductive solid electrolyte layers 131, 121.

An advantage of feature (C) is that accurate measurement is attained by preventing oxygen-ions from leaking across the solid electrolyte layers 131, 121. Without such an ion-leakage preventing ceramic spacer 143, when the oxygen-pumping cell 12 pumps oxygen from or into a diffusion space 141, the second oxygen-ion conductive layer 12 leaks its oxygen-ions into the first oxygen-ion conductive layer 131, causing erroneous measurement of electromotive force produced across an oxygen-detecting electrodes 133 and a reference electrode 136 of the oxygen-detecting cell 13.

A preferable material for the ion-leakage preventing ceramic spacer 143 is alumina or alumina containing less than 20% by weight of zirconia. This is partly because the alumina grains are included in the first and second solid electrolyte layers 131, 121 so as to match a thermal expansion thereof to the alumina substrate 11, partly because the alumina per se does not greatly harm internal resistance of the oxygen-pumping cell 12 comprising zirconia while other material such as silica does, and further because a voltage is applied across electrodes 123, 126 of the oxygen-pumping cell 12 in order to independently measure an oxygen-pumping ionic current flowing across the electrodes 123, 126. Notably, this oxygen-pumping ionic current is used as an indicator of combustion state (fuel-rich to lean) of the exhaust gas.

(D): A gas-diffusion space 141 is formed between an electrode 133 of the oxygen-detecting cell 13 and an electrode 126 of the oxygen-pumping cell 12, advantageously featuring a distance therebetween of 20–80 micrometers. This gas-diffusion space is necessary for a full range air-fuel ratio sensor, a NOx sensor for detecting nitrogen oxide, etc. In a fuel-rich condition (i.e., an oxygen-scarce state), the amount of oxygen pumped into the gas diffusion space 141 until when a predetermined oxygen partial pressure is detected by the oxygen-detecting cell 13 is measured. In a fuel-lean condition (i.e., an oxygen-abundant state), the amount of oxygen pumped out of the oxygen space 141 until when the predetermined oxygen partial pressure is detected by the oxygen-detecting cell 13 is measured. In this way, the oxygen amount pumped into or pumped out of the gas diffusion space 141 indicates the combustion state (rich to lean) of an internal combustion engine. If the distance is more than 80 micrometers, the temperature difference between the oxygen-detecting cell 13 and the oxygen-pumping cell 12 becomes too large. This results in erroneous measurement of an amount of the gas of interest, and in addition, the oxygen-pumping cell 121 looses its pumping capability. If the distance is less than 20 micrometers, the measurement amount of, for instance the exhaust gas is too limited or insufficient resulting in erroneous or inaccurate measurement of the gas amount.

(E): A laminate of the alumina substrate 11, the first and second oxygen-ion conductive solid electrolyte layers 131, 121, and the ion-leakage prevention spacer 143 is co-fired or rather simultaneously sintered, such that the second oxygen-ion conductive solid electrolyte layer 121 that partly constitutes the oxygen-pumping cell 12 and contains zirconia and alumina is laminated on the ion-leakage preventing ceramic spacer 143, the alumina substrate 11 embedding a heating resistor for heating or activating the second oxygen-ion conductive solid electrolyte layer 121 is laminated on the first oxygen-ion conductive solid electrolyte layer 131 that partly constitutes the oxygen-detecting cell 13, and the ion-leakage preventing ceramic spacer 143 for preventing oxygen-ions from leaking from the second oxygen-ion conductive solid electrolyte layer 121 to the first oxygen-ion conductive solid electrolyte layer 131 is laminated between said first and second oxygen-ion conductive solid electrolyte layers 131, 121.

An advantage of the co-fired laminate (1a) is dimensional compactness or size reduction of the gas sensor. The co-fired laminate improves thermal conduction of heat from the heating resistor 115 to the oxygen-pumping cell 12, heating efficiency of the heating resistor 115 for activation of the oxygen-detecting cell 13 and oxygen-pumping cell 12 and electric power consumption by the heating resistor 115, compared to a non-co-fired laminate.

Co-firing as used herein means simultaneously firing or sintering a green (unfired) laminate comprising a green alumina substrate and green oxygen-ion conductive solid electrolyte layers under a common firing condition.

(F): An ionic migration-preventing electrode 117 for preventing deterioration and/or electrical disconnection of the heating resistor 115 is advantageously embedded or incorporated in the alumina substrate 11, wherein the electric potential of said ionic migration-preventing electrode 117 is equal to or lower than the lowest electric potential of any part of the heating resistor 115.

So long as the electric potential of the ionic migration preventing electrode 117 is maintained equal to or lower than that of any portion of the heating resistor 115, no metal ions migrate toward the heating resistor 115 under a voltage applied across the heating resistor 115 at high temperature. The ionic migration-prevention electrode 117 draws or gathers the migrating metal ions, and vicariously protects the heating resistor 115 from electrochemical deterioration or electrical disconnection by the migrated metal ions. Notably, this ionic migration occurs especially at a high exhaust gas temperature of more than 700° C. At such high temperature, the metal ions including alkaline and/or alkaline earth metal ions such as Mg and Ca constituting inorganic binders such as MgO and CaO contained in the alumina substrate 11 or in a bonding material for the alumina substrate 11 and the oxygen ion-ion conductive solid electrolyte layer 131 migrate through the alumina substrates and gather around the lowest electric potential portion.

(G): Specifically, the electric potential to be applied at the ionic migration-preventing electrode 117 is maintained to be equal to or lower than an electric potential at a position connecting the heating resistor 115 and leads 116 of the heating resistor 115. Since the leads 116 are designed to be wider or thicker in width or thickness than the heating resistor 115 and the temperature of the leads 116 is lower than the heating resistor 115, the electrical disconnection of the leads 116 would not occur even if some metal ions migrate or gather around one of the leads 116.

(H): The ionic migration-preventing electrode 117 is importantly positioned between the heating resistor 115 of the oxygen concentration cell 13 and an outer surface of the alumina substrate 11. In other words, the ionic migration-prevention electrode 117 incorporated or embedded in the alumina is most preferably placed between the heating resistor 115 and the oxygen-ion conductive solid electrolyte layer 131, according to an aspect of the invention.

Since the migrated ions gather around the ionic migration preventing electrodes 117 and combine with oxygen newly forming a glassy phase around the ionic migration-preventing electrode 117, the alumina ceramic 11 surrounding the ionic migration preventing electrode 117 is weakened or degraded in strength. Since such a degrading glassy phase which is low in insulating ability is easily formed inside the alumina substrate 11 that normally contains a considerable amount of the inorganic binder, cracks tend to occur where the glassy phase is formed inside the alumina substrate 11, in addition to insulation failure between the heating resistor 115 and the reference electrode 136 of the oxygen-detecting cell 13. In a worst case when an ionic migration-preventing electrode 117 is positioned between the heating resistor 115 and the oxygen-detecting cell 13, the heating resistor 115 might be separated from the oxygen-detecting cell 13, or a serious problem such as a sensor malfunction and loss of control in an actual exhaust gas control system would arise due to insulation lost between the heating resistor 115 and the oxygen detecting cell 13.

In the case, according to an aspect of the invention, when the ionic migration-preventing electrode 117 is disposed between the heating resistor 115 and the outer surface of the alumina substrate 11 such that the degrading glassy phase to be formed around the ionic migration-preventing electrode 117 is formed near or at the outer surface of the alumina substrate 11 on which surface the oxygen-detecting cell 13 is not laminated, even if cracks occur due to the glassy phase newly formed by the migrated metal ions, the heating resistor 115 that performs an important role for activating the sensor cells 13, 12 does not separate from the oxygen-detecting cell 131 and the sensor will not malfunction nor lose accuracy in measuring the gas amount.

Another advantage of the feature (H) is that quick activation of the sensor or rather quick transfer of thermal energy from the heating resistor through the oxygen-concentration cell 13 to the oxygen pumping cell 12 is attained, since the ionic migration preventing electrode 117 is not positioned between the heating resistor 115 and thereby the glassy phase that slows thermal transfer is not newly formed therebetween.

This feature (H) characterized in that an ionic migration-preventing electrode 117 is positioned between a heating resistor 115 and an outer surface of an substrate 11, can be applied to any high temperature gas sensor having a laminate of an oxygen-ion conductive solid electrolyte constituting an oxygen-detecting cell and an alumina substrate embedding a heating resistor.

(I): The second oxygen-ion conductive solid electrolyte layer 121 contains alumina in an amount less than that of the first oxygen-ion conductive electrolyte layer 131. In other words, the content of the alumina contained in the first oxygen-ion conductive solid electrolyte layer 131 is higher than that of the alumina contained in the second oxygen ion conductive solid electrolyte layer 121.

Advantage of this feature (I) is focused on prevention of possible fracture of the oxygen-pumping cell 12 during the time at which the heating resistor 115 is forced to quickly elevate the temperature of the oxygen-pumping cell 12 through the oxygen-detecting cell 13. This fracture may be accompanied by "blackening" or reduction (deoxidization)

of the second oxygen-ion conductive solid electrolyte layer 121 when the temperature difference between the two laminated cells 13, 12 is too large or when the temperature-elevating transient period such as after activation of the cells 13, 12 is started at a very cold temperature. When the sensor laminate (1a) comprising the two cells 13, 12 is very cold and needs to be heated quickly for activation by the heating resistor 115, the oxygen-detecting cell 13 that is closer to the heating resistor 115 reaches its activation temperature faster than the oxygen-pumping cell 12 does. The oxygen-detecting cell 13 electrically requests or orders the oxygen-pumping cell 12 to pump in or pump oxygen out of the gas diffusion space 141 through a control circuit, even if the oxygen-pumping cell 12 is not fully activated and not ready to pump oxygen. This is when the oxygen-pumping cell 12 deprives oxygen ions from the zirconia of its oxygen-ion conductive solid electrolyte layer, instead of pumping oxygen of the diffusion space 141, and causes "blackening" or reduction of the oxygen-ion conductive solid electrolyte layer 121 constituting the pumping cell 12 and possibly fractures the oxygen-pumping cell 12.

A higher content of alumina in the first oxygen-ion conductive solid electrolyte layer 131 advantageously increases the internal resistance of the oxygen-detecting cell 13 so that it is higher than that of the oxygen-pumping cell 12, and slows down or paces down the activation of the oxygen-detecting cell 13 so as to match it with that of the oxygen-pumping cell 12. This matching of activation between the two cells 13, 12 incorporated in the sensor laminate (1a) is advantageously attained and stabilized by inclusion of more alumina into the first oxygen-ion conductive electrolyte layer 131 than into the second oxygen-ion conductive solid electrolyte layer 121, since a feedback control circuit is used across the cells 13, 12, based on a temperature measured based on the internal resistance of the oxygen-detecting cell.

(J): Specifically, the amount of alumina contained in the oxygen-ion conductive solid electrolyte layer 121 that constitutes the oxygen pumping cell 12 is less by at least 5% by weight, or preferably less by at least 10% by weight, than that of the alumina contained in the oxygen-ion conductive solid electrolyte layer 131 constituting the oxygen-detecting cell 13.

An advantage of this feature (J) is similar to those described for the above feature (I), but the advantage becomes more remarkable when the first oxygen-ion conductive solid electrolyte layer 131 contains 10 to 80% by weight of alumina and 20 to 90% by weight of zirconia.

Further advantage of this feature (I) is that measurement of the electromotive force produced across electrodes 133, 136 of the first oxygen-detecting cell 13 becomes more stable than measurement of the same across an oxygen-detection cell that uses an oxygen ion conductive electrolyte layer containing substantially no alumna or rather containing less than 5% by weight of alumina. This is because the increase of the internal resistance of the first oxygen-detecting cell 13 thus realized stabilizes measurement of the electromotive force produced by the oxygen detecting cell 13, the electromotive force actually being measured as a voltage detected across a outer resistor attached across the oxygen detecting cell 13.

Preferably, the second oxygen-ion conductive solid electrolyte layer 121 that constitutes the oxygen-pumping cell 12 contains 60–90% by weight of zirconia and 10–40% by weight of alumina, while the first oxygen-ion conductive solid electrolyte layer 131 that constitutes the oxygen-detecting cell 12 contains preferably 40–80% by weight of zirconia and 20–60% by weight of alumina.

Specifically, the second oxygen-ion conductive solid electrolyte layer 121 that constitutes pumping cell 12 contains alumina in an amount less by 10–50% by weight than the first oxygen-ion conductive solid electrolyte layer that constitutes the oxygen-detecting cell 131.

(K): The first and second oxygen-ion conductive solid electrolyte layers 131, 121 contain 10–80% by weight of alumina, respectively, and the average grain size of alumina contained in the first and second oxygen-ion conductive solid electrolyte layers 131,121 is less than 1 micrometer.

An advantage of this feature (K) is effective prevention of a phase transformation of zirconia contained in the laminated oxygen-ion conductive solid electrolyte layers 131, 121 in an actual thermal cycling environment, and prevention of cracks induced in the sensor laminate (1a) due to thermal expansion difference between the laminated solid electrolyte layers 131, 121 and the alumina substrate 11. This feature (K) is important to the second oxygen-ion conductive solid electrolyte layer 121 that constitutes the oxygen-pumping cell 12. Finer alumina grains better prevent the phase transformation of the partially stabilized zirconia in the second oxygen-ion conductive solid electrolyte layer 121.

(L): The zirconia included in the second oxygen-ion conductive solid electrolyte layer 121 is a partially or wholly stabilized zirconia. Preferably, zirconia that substantially consists of a partially stabilized zirconia with a phase (or phases) of the zirconia substantially consisting of tetragonal and cubic phases, containing no monoclinic phase or rather less than 5% by weight of a monoclinic phase, is used in the first and second oxygen-ion conductive solid electrolyte layers 131, 132.

An advantage of this feature (L) is strength and endurance (or rather durability) of the two cells 13, 12 in a practical thermal cycling environment. If a monoclinic phase of zirconia is contained substantially (more than 5% by weight) in the oxygen-ion conductive layers 131, 121, a zirconia phase transformation reversibly occurs from monoclinic to tetragonal under thermal cycling and thereby micro-cracks or structural weakness of the first and second oxygen-ion conductive solid electrolyte layers 131, 121 that are co-fired and multi-layered with the alumina substrate 11 appears. Although the thermal expansion coefficient of the monoclinic phase is lowest among the cubic, tetragonal and monoclinic phases and is lower than that of alumina, use of the monoclinic phase as an adjuster for thermal expansion difference between the alumina substrate and the solid electrolyte layers 121, 131, especially use thereof in the second-oxygen ion conductive solid electrolyte layer 121 of the oxygen-pumping cell 12, is avoided because the monoclinic to tetragonal phase transformation is detrimental to durability of the sensor laminate (1a). Without the alumina grains, the reversible monoclinic to tetragonal phase transformation occurs at a temperature of more than 900 degrees centigrade, and the tetragonal to monoclinic phase transformation occurs under the thermal cycling environment at more than 200 degrees centigrade.

A preferable phase ratio of cubic phase to tetragonal phase formed in zirconia of the solid electrolyte layers 131, 121 is from 1:4 to 2:1, more preferably from 1:3 to 3:1, or most preferably 3:7 to 1:1. The optimum phase ratio varies, depending on an amount of the alumina included in the zirconia electrolyte layers 131, 121. In this phase ratio range formed with the alumina grains and partially stabilized zirconia, a phase transformation of zirconia from tetragonal to monoclinic, otherwise drastically occurring at a temperature of more than 200 degrees centigrade (Celsius) especially under a humid environment, is effectively suppressed, according to an aspect of the invention. The phase transformation (also called a phase transition) between tetragonal and monoclinic phases accompanies a volume change of zirconia per se, and is detrimental to the strength and durability of the sensor laminate (1a). The above phase ratio can be determined by a known method, e.g., by analyzing the values of X-ray diffraction peak intensity with respect to monoclinic, tetragonal phase and/or cubic phase.

(M): A reference electrode 136 that constitutes the oxygen-detecting cell 12 and directly faces the alumina substrate 11 is a porous electrode capable of storing oxygen therein. The stored oxygen can be used as referential oxygen with its partial pressure controlled to be constant by flowing a very small current across the electrodes 133, 136. Excess stored oxygen in the porous electrode is ventilated outside the sensor laminate (1), through a porous lead 127 thereof that is led to outside the laminate (1a). An advantage of this feature is that substantially only oxygen can be designed to pass through lead 137 of the reference electrode that works as channel (16) for ventilating oxygen outside the sensor laminate (1a). This lead 137 per se works as a channel (16) for draining or ventilating oxygen. Contaminants such as water do not reach the reference electrode to affect the function of the reference electrode 136 because the oxygen partial pressure of the oxygen in the reference electrode can be elevated by the small current flowing across the electrodes 133, 136. With this feature is incorporated in the laminate, accurate measurement is improvingly attained.

(N): Reduction-preventing insulative layers 128,138 are importantly provided between the leads 127,124 of the oxygen-pumping cell 12 and the oxygen-ion conductive solid electrolyte layer 121.

An advantage of feature (N) is prevention of the second oxygen-ion conductive layer 121 from reduction (or rather deoxidization) of zirconia contained in the second oxygen-ion conductive solid electrolyte layer 121 surrounding the leads 127, 124. Without such a reduction-prevention insulative layer, deoxidization of zirconia occurs since a voltage is applied across the leads 124, 127 in order to pump oxygen in or out of the diffusion space 141 by the oxygen-pumping cell 12. Notably, "blackening" (i.e., deoxidization) occurs around the electrode 127 in a fuel-lean state and occurs around the electrode 124 in a fuel-lean state, depending on the applied voltage polarity. The insulative layer 128 preferably comprises alumina.

Another reduction-preventing insulative layer 138 may be provided between the lead 134 of the oxygen-detecting cell 13 and the solid electrolyte layer 131. Although the lead 134 thereof is not so seriously reduced or deoxidized as compared to the leads 124, 127 of the oxygen-pumping cell 12, accurate measurement of electromotive force detected across the detecting electrode 133 and the reference electrode of the oxygen-detecting cell 13 is improved.

(O): The alumina substrate 11 in which the heating resistor 115 is embedded contains at least 99% or preferably 99.9% by weight of alumina.

Feature (O) becomes very advantageous in preventing deterioration or electrical disconnection of the heating resistor 115 and in decreasing formation of the glassy phase weakening the alumina substrate 11. An advantage of feature (O) is that the need for a costly platinum ionic migration-preventing electrode 117 can be eliminated. Another advantage is size compactness of the laminate (1a) and thermal transfer efficiency of heat generated by the heater 115 thorough the alumina substrate 11.

(P): A reinforcing insulative cover 152 that reinforces the second oxygen ion-conductive layer 121 and protects the lead 124 of the oxygen-pumping cell 12 is used. This feature (P) is advantageous in terms of endurance or durability of the lead 124 and structural strength of the sensor laminate (1a).

(Q): The thickness of the first oxygen-ion conductive solid electrolyte layer 131 constituting the oxygen-detecting cell 13 is advantageously 10–200 micrometers, and the thickness of lead 137 of the electrode 136 located between the oxygen-ion conductive solid electrolyte layer 131 and the alumina substrate 11 is advantageously 1–20 micrometers or preferably 8–18 micrometers. This feature (Q) leads to an advantage of size compactness and preventing cracks of the electrolyte layer 131 as well as assurance of reliable oxygen-detecting function of the oxygen-detecting cell 13.

(R): The thickness of the second oxygen-ion conductive solid electrolyte layer 121 constituting the oxygen-pumping cell 12 is importantly 30–400 micrometers. Since the oxygen-pumping cell 12 is formed outside the oxygen-detecting cell 12 and forming the diffusion space 141 inside, the minimum thickness of 30 micrometer is necessary for structural strength. However, if the thickness exceeds 400 micrometers, de-lamination of the solid electrolyte layer 121 from the alumina substrate 11 is induced due to inconsistency of thermal dissipation. This feature (R) leads to reliability of the two-cell type gas sensor and prevents cracking of the electrolyte layer 121 as well as lends endurance of the oxygen-pumping function of the oxygen-pumping cell 13.

(S): A gas-diffusion passage 142 having a predetermined resistance controlling an amount of the molecules of gaseous components entering the gas diffusion space 141 is advantageously formed between the gas diffusion space 141 and the measurement gas outside the sensor laminate (1a). Specifically, when this gas diffusion passage 142 is formed between the first and second oxygen-ion conductive solid electrolyte layers 131 and 132, it is easy to adjust the predetermined resistance and to make a high quality sensor laminate (1a).

(T): The area of electrode 133 of the oxygen-detecting cell 13 is 15 to 80% of that of the electrode 126 of the oxygen-pumping cell 126. This feature (T) is advantageous in optimizing the internal resistance of the oxygen-detecting cell 13 and in effectively detecting the amount or concentration of oxygen inside the diffusion space 141 as a function of the temperature of oxygen-detecting cell 13.

Among these features (A)–(T), the most important features are (A), (B), (F), (H), (I), (J), (K), (L), (O) and/or a combination thereof.

DESCRIPTION OF THE PREFERRED EMBODIMENTS

Figure 1:
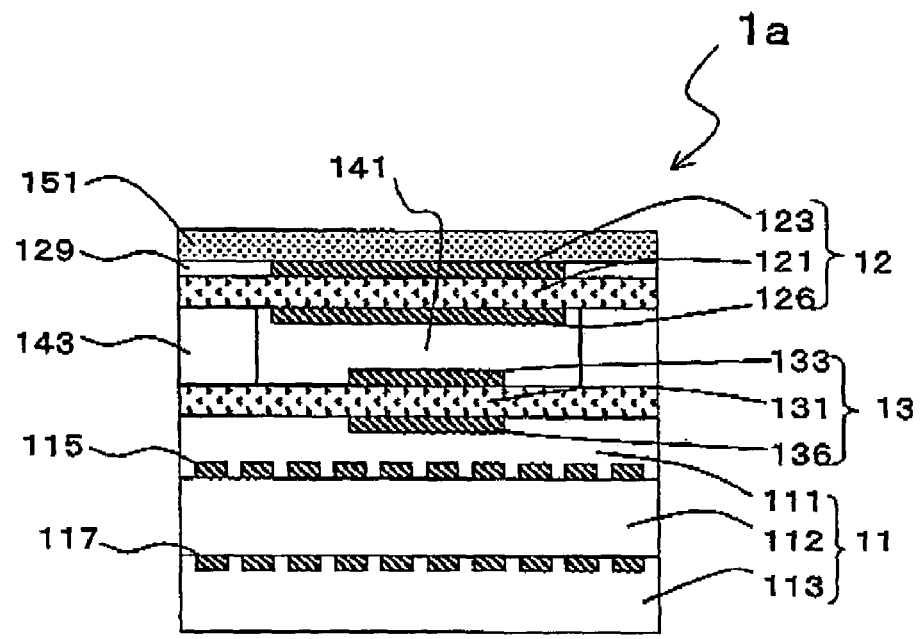
FIG. 1 is a schematic transverse sectional view of a gas sensor comprising a laminate of two sensor cells and an alumina substrate, according to the present invention.
Figure 2:
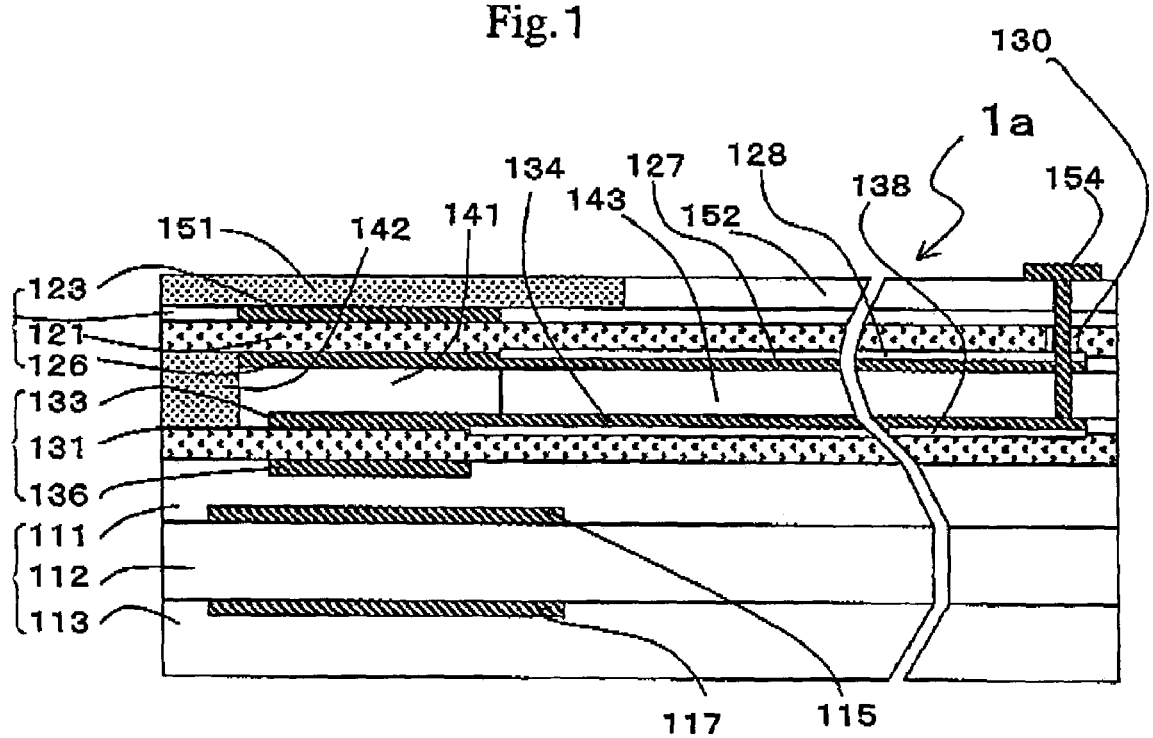
FIG. 2 is a schematic longitudinal sectional view of the gas sensor shown in FIG. 1, as sectioned along a longitudinal center of the gas senor.

The gas sensor embodied according to the invention will be described in detail by reference to the drawings. However, the present invention should not be construed as being limited thereto. Referring to FIGS. 1 and 2, the gas sensor has a sensor laminate (1a) comprising at least three major laminated components; i.e., an alumina substrate 11 embedding a heating resistor 115 and two oxygen-ion conductive electrolyte layers 131, 121 respectively constituting an oxygen-detecting cell 13 and an oxygen-pumping cell 12.

In an aspect of the invention, the sensor laminate (1a) has a structure such that the first oxygen-ion conducting solid electrolyte layer 131 constituting the oxygen-detecting cell 13 is co-fired between the alumina substrate 11 and the second oxygen-ion conductive solid electrolyte layer 121 constituting the oxygen-pumping cell. In other words, the heating resistor 115 firstly activates the oxygen-detecting cell 13 and then the oxygen-detecting cell 13 activates the oxygen-pumping cell 12. Since a comparatively large ionic current flows through the oxygen-pumping cell 12 and therefore the oxygen-pumping cell is more vulnerable than the oxygen-detecting cell 13 in a practical thermal cycling environment, the oxygen-detecting cell works advantageously as a thermal buffer for buffering a sharp temperature increase of the oxygen-pumping cell 12 by the heating resistor 115.

One of the important components laminated into the laminate (1a) by co-firing is an alumina substrate 11 in which a heating resistor 115 for heating and activating the oxygen-detecting cell 13 and the oxygen pumping cell 12 is embedded and optionally an ionic migration-prevention electrode 117 for preventing the heating resistor 115 from electrical degradation and/or electrical disconnection is embedded. The other important components laminated in the laminate (1a) by co-firing are an oxygen-pumping cell 13 and an oxygen-detecting cell 12, in which cells 12, 13 alumina grains are contained. Since the alumina grains are contained in the oxygen-pumping cell electrolyte 121 having a phase substantially consisting of cubic and tetragonal phases, a phase transformation from tetragonal to monoclinic is greatly prevented.

The alumina substrate 11 may be comprised of first, second and third co-fired alumina layers 111, 112, 113. As understood from FIG. 3, the heating resistor 115 and two leads 116 thereof, which are made mainly of platinum, are disposed between the first and second alumina layers 111, 112, and co-fired therewith. The leads 116 of the heating resistor 115 are electrically connected to the outer terminal 156(−) 157(+) formed on an outer surface of the third alumina layer 113 via two through-holes penetrating the alumina layers 112, 113.

The ionic migration-preventing electrode 117 that is also made mainly of platinum is disposed between the second and third alumina layers 112, 113 and co-fired therewith. One end of the ionic migration-preventing electrode 117 is electrically connected to the outer terminal pad 156(−) of negative polarity, but the other end thereof is not connected to any terminal. The ionic migration-preventing electrode 117 has a meandering line, but it can be straight.

When two alumina layers are used, the heating resistor 115, the leads 116 thereof and the migration-preventing electrode 117 may be disposed between the first and second alumina layers 111, 112 so that the third alumina layer 113 may be eliminated.

Notably, two types of gas sensors that do not cause a serious problem relating to metal-ion migration are provided according to the present invention; one type requires a high-purity alumina ceramic with the purity thereof being more than 99%, or more preferably more than 99.9%, for use in the alumina substrate, and the other type requires an ionic migration prevention electrode regardless of the purity of the alumina ceramic constituting the alumina substrate.

The heating resistor 115 embedded in the alumina substrate 11 is necessary for all types of the gas sensors and a combination thereof. As understood from FIG. 3, a meandering line made mainly of platinum for the heating resistor 115 and two straight leads thereof 116 that have a wider line width than the meandering line are embedded in the alumina substrate 11 and are sandwiched by the first and second alumina layers 111, 112. One end of each the leads 116 is connected to an end of the meandering line of the heating resistor 115 positioned close to an end of the rectangular-shaped alumina substrate 11. The other end of each the leads 116 is extended to two through-holes formed close to the other ends of the second and third alumina layers 112 and 113, and is electrically connected to either the negative and positive terminal pads 156(−), 157(+) that are formed on an outer surface of the third alumina layer 113. Electric power of 13–14 d.c.v. is normally applied across the terminal pads 156 (−), 157(+) so that the heating resistor 115 generates heat or thermal energy. The electrical resistance of the heating resistance is preferably designed to be about 3 Ω.

An ionic migration-preventing electrode may be optionally incorporated in the laminate (1a) according to one aspect of the invention. A line made of mainly of platinum for the ionic migration-preventing electrode 117 is formed between the second and third alumina layers 112 and 113, by straightly wiring from a negative outer pad 156 (−) along the lead 116 with negative polarity of the heating resistor 115, meandering through an area where the corresponding meandering line of the heating resistor 115 is correspondingly formed and insulated by the second alumina layer 112 from the migration preventing electrode 115, straightly wiring along the lead 116 with positive polarity of the heating resistor 115 and ending at a corresponding middle position of the lead 116 of positive polarity.

The entire line of the ionic-preventing electrode 117 is charged with negative polarity, since it is electrically connected only to the outer terminal 156(−) of negative polarity. As a result, metal ions that are electrically positive are drawn to the ionic-preventing electrode 117 of negative polarity.

Specifically, the electric potential of the line of the ionic preventing electrode may be designed to be equal to or lower than that of the line of the heating resistor that is comparatively narrow in width and vulnerable. Practically, the ionic migration-preventing electrode 117 is connected to a portion of the leads 116 of negative polarity, the portion being lower than the heating portion in electric potential. Metallic ions such as Na and K, and Ca, Ba and Mg having a valence of two or three and normally forming oxides as an insulating inorganic binder for alumina grains or contaminants at a low temperature become chemically unstable in a high temperature exhaust gas ambient. These species migrate to seek a chemically stable position with respect to their chemical equilibrium balanced by electric potential, temperature, etc., and move to separate from the oxygen of the oxide in a high temperature ambient. Instead of the heating resistor 115, the ionic migration-preventing electrode provides such a stable position for metal ions to gather, and at which position the migrated metal ions can bind with oxygen from the ambient gas to form a new glassy phase when the ambient gas temperature is cooling down, since they do not return to their original position.

Without the migration-preventing electrode, the migrated metal ions cause various serious problems such as electrically disconnecting the heating resistor 115 by volume increase of the glassy phase around the resistor 15 and weakening the alumina substrate 11.

The ionic migration-preventing electrode 117 gathers the migrating metal ions instead, thereby vicariously protecting the heating resistor 115 from the metal ions migrating toward the heating resistor 115 so that the glassy phase causing the various problems is not formed around the vulnerable heating resistor 115. This is the reason why the electric potential of the ionic migration-preventing electrode should be maintained equal to or lower than that of the heating resistor in an aspect of the invention. In other words, the electrical potential of the ionic migration-preventing electrode 117 should be equal to or lower than the electric potential at a position connecting the heating resistor 115 and leads 116 of the heating resistor 115.

In another aspect of the invention, the position of the ionic migration-preventing electrode also becomes important, if the ionic migration-preventing electrode is used in a laminate (1a). This is because a new glassy phase is inevitably formed around the ionic migration-prevention electrode. Since the new glassy phase weakens the strength of the alumina ceramic surrounding the migration-prevention electrode, the position where the glassy phase can be allowed to form needs to be carefully designed, from the view-points of reliability, endurance, size compactness, heating efficiency of the heating resistor and activation of the sensor cells.

In an aspect of the invention, the ionic-migration-prevention electrode 117 for preventing the heating resistor 115 from degradation or electrical disconnection is formed or disposed, not between the heating resistor 115 and the electrode 136 of the oxygen-detecting cell 13 (or any electrode 133, 126, 123, regardless of the position of the cells 12, 13). Since the electric potential of the migration-preventing electrode 117 is lower than that of the heating resistor 115, the metal ions migrate toward the migration-prevention electrode 117 and form the glassy phase around the ionic migration-preventing electrode 117. In other words, a new glassy phase or new glass formed by migrated metal ions around the migration-prevention electrode 117 should not be formed between the heating resistor 115 and any electrode of cells 12, 13.

In the case that the migration-prevention electrode and the heating resistor is formed on the same plane, for instance, as sandwiched by the first and second alumina layers 111, 112, an electric line of the heating resistor should run far away as possible from the electrode 136 of the oxygen-detecting cell 13 and a line of the heating resistor such that the new glassy phase is formed closer to an outer surface of the alumina substrate 11 than to the electrode 136 of the oxygen detecting cell 13. In this manner, both the cell electrode 136 and the heating resistor are protected from the new glassy phase.

Platinum or platinum-containing material is used for these electrical wirings of the ionic migration prevention electrode 117 and the heating resistor 115 including the leads 116 thereof, and for those electrodes 133, 136, 123, 126 of the oxygen-detecting cell 13 and the oxygen-pumping cell 12 including the leads 134, 137, 124, 127, and for the outer terminal pads 153, 154, 155, 156. This is because platinum can be co-fired in an oxidizing atmosphere in which the alumina substrate and the zirconia layers are co-fired, for instance at a temperature of about 1450–1560 degrees centigrade.

Alumina-containing material is used at least for the alumina substrate 11, the ion-leakage prevention spacer 143, the reduction-preventing layers 128, 129, 138 and the oxygen-ion conductive solid electrolyte layers 121, 131. This is because improved quick activation of the oxygen-detecting cell 13 and the oxygen-pumping cell 12 is attained.

The alumina layers 111, 112, 113 constituting the alumina substrate 11, may contain up to 30% by weight of a heterogeneous metal oxide material such as silica, magnesia and calcia, other than alumina, or may be bonded by firing with such a heterogeneous material, so long as the ionic migration-preventing electrode 117 is incorporated in the alumina substrate 11. However, oxides of alkaline and alkaline earth metal should be minimized if they have to be added as an inorganic binder into the alumina substrate 11.

The alumina content may be varied or different from each other among the first, second and third alumina layers 111, 112, 113 from view points of heating efficiency by the heating resistor 115 for the cells 12, 13, prevention of metal ions from migrating through the alumina substrate 11 and/or co-firing conditions with the cell electrolyte layer 131. A typical alumina substrate containing 4% by weight of silica, 3% by weight of MgO and 1% by weight of calcia needs the ionic-migration-preventing electrode 117.

When the content of the alumina in the first and second alumina layers 111, 112 that sandwich or surround the heating resistor 115 is more than 99% by weight, or preferably more than 99.9% by weight (in other words, when the content of the heterogeneous metal oxide material contained in the alumina layers 111, 112 other than alumina is not more than 1% by weight, or preferably not more than 0.1% by weight), the ionic migration of metal ions is greatly decreased. As a result, the ionic migration-preventing electrode for preventing the heating resistor 115 from degradation or electrical disconnection may be eliminated. Most preferably, when the heterogeneous material contained in the alumina layers 112, 113 is less than 0.01% by weight, the ionic migration is completely shut out and the ionic migration-preventing electrode 117 is unnecessary.

Figure 3:
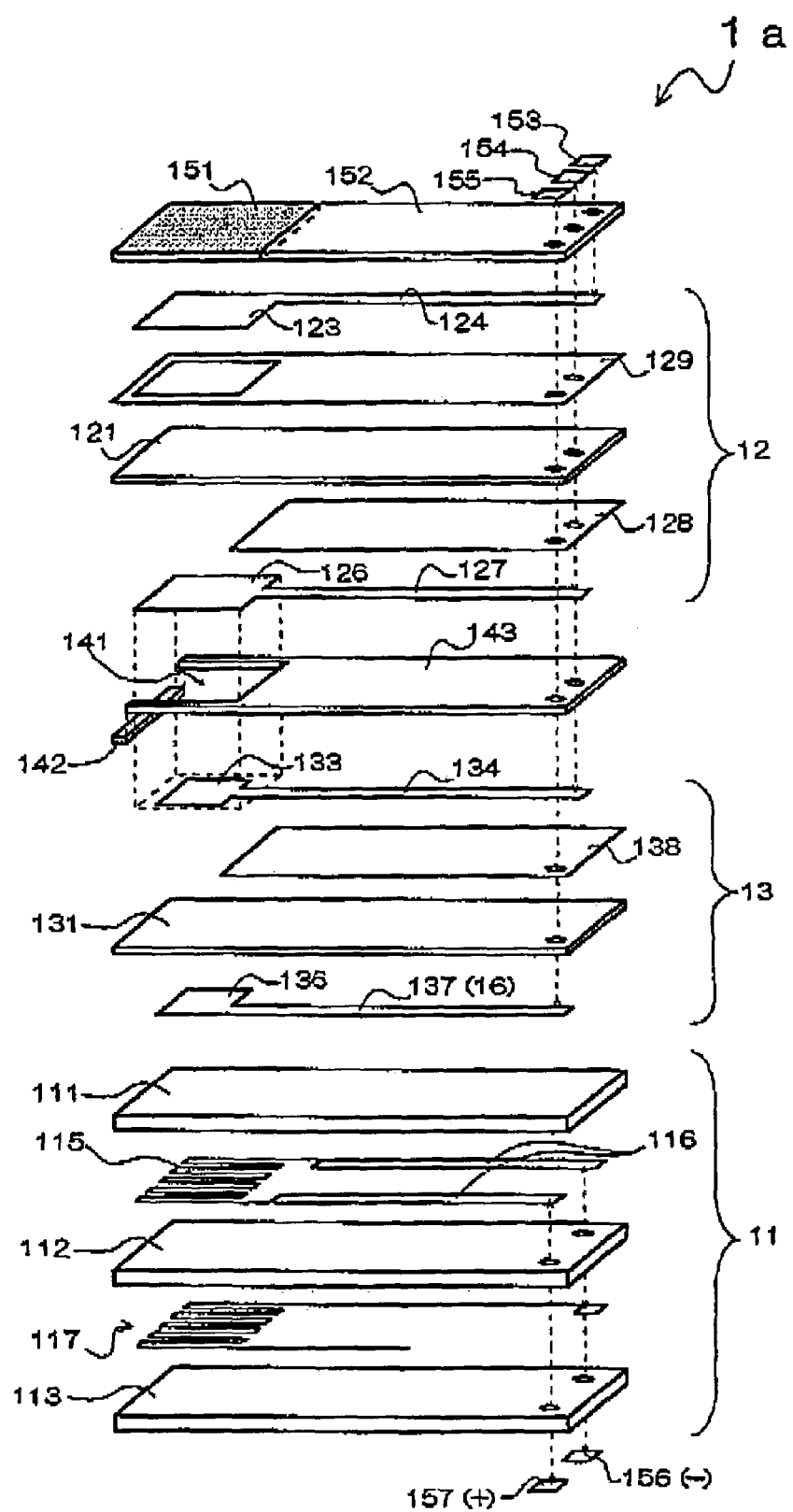
FIG. 3 is a schematic perspective view of the gas sensor shown in FIGS. 1 and 2, showing its constituent components.

Referring to FIG. 3, a portion of the first oxygen-ion conductive solid electrolyte layer 131 that is co-fired with the alumina substrate 11 constitutes the oxygen-detecting cell 13. The first oxygen-ion conductive solid electrolyte layer 131 is of a rectangular shape with a through-hole formed near a corner formed by a longitudinal side end and distal end thereof.

The lead 137 formed extendedly from an oxygen-reference electrode 136 and closely along the longitudinal side of the first oxygen-ion conductive solid electrolyte layer 131 is further extended so as to electrically connect to a first outer pad 155 formed on a surface of a reinforcing insulative cover layer 152 via a through-hole penetrating the first and second solid electrolyte layers 131, 121, reduction-preventing insulative layers 138, 128, 129, an ion leakage preventing ceramic spacer 143 and the reinforcing insulative layer 152.

The oxygen-detecting electrode 133 of the oxygen-detecting cell 13 is formed and co-fired between the first oxygen-in conductive solid electrolyte layer 131 and the first alumina layer 111. The lead 134 connecting one end thereof to the oxygen-detecting electrode 133 and connecting the other end thereof to a second outer terminal 154 is cofired between a reduction-preventing insulative layer 138 and an ion-leakage preventing ceramic spacer 143. The lead 134 runs along a longitudinal center of the first oxygen-ion conductive solid electrolyte layer 131 to a distal end portion of the first electrolyte layer 131 so as to be connected electrically the second outer pad 154 formed on the reinforcing insulative layer 152 via a through-hole penetrating the ion-leakage preventing ceramic spacer 143, first and second reduction-preventing insulative layers 128, 129 and a reinforcing insulative layer 152.

The oxygen-reference electrode 136 and an oxygen-detecting electrode 133 are cofired on different faces of the oxygen-ion conductive solid electrolyte layer 131, respectively, so as to constitute the oxygen-detecting cell 13. The oxygen-detecting electrode 133 and the oxygen-reference electrode 137 of the oxygen-detecting electrode 13 are positioned to correspond to the position of the heating resistor 115 that in turn is positioned beneath the first alumina layer 111.

The first oxygen-ion conductive solid electrolyte layer 131 interfaces with the first alumina substrate 111, the oxygen-reference electrode 136 and the lead 137 thereof, and also interfaces with the oxygen-detecting electrode 133 of the oxygen-detecting cell 13 and the reduction-preventing insulative layer 138.

The first oxygen-ion conductive solid electrolyte layer 131 contains zirconia and alumina. Preferably the amount of alumina in the first oxygen-ion conductive solid electrolyte layer 131 is 10–80% by weight, and more preferably 20–60% by weight, based on 100% by weight of the entire first solid electrolyte layer.

Notably, high purity alumna of more than 99% purity or preferably 99.9% purity with a particle size of less than 1 micrometers should be contained at least in the second oxygen-ion conductive-solid electrolyte layer 121 for the oxygen-pumping cell 12 and optionally, yet preferably in the oxygen-ion conductive solid electrolyte layer 131 for the oxygen-detecting cell 13. This is from a view point of lowering internal resistance of the oxygen-pumping cell 12 and control of zirconia phase so as not to transform to monoclinic phase.

The zirconia used in the oxygen-solid electrolyte layer 121 laminated in the laminate (1*a*) is a partially stabilized zirconia substantially consisting of tetragonal phase and cubic phase with substantially no monoclinic phase. The finer the average grain size of alumina grains that is used, the better structural strength and stability against phase transformation from tetragonal to monoclinic is attained in a thermal cycling under high humidity, when the average grain size of zirconia is less than 2.5 micrometers, as measured by a known method using a scanning electron microscope (SEM) such as that described in EP 1026502A2. This is because fine alumina grains existing at grain boundaries of zirconia suppress grain growth and phase-transformation of zirconia.

The zirconia included in the first and second oxygen-ion conductive solid electrolyte layers 131, 121 is a partially stabilized zirconia, for instance, partially stabilized by 2–9 mol % of yttria. Preferably, a partially stabilized zirconia with its phase (or phases) substantially consisting of tetragonal and cubic phases, containing no monoclinic phase or rather less than 5% by weight, is used in the first and second oxygen-ion conductive solid electrolyte layers 131, 132.

A preferable phase ratio of cubic phase to tetragonal phase formed in zirconia of the solid electrolyte layers 131, 121 is from 1:4 to 2:1, more preferably from 1:3 to 3:1, or most preferably 3:7 to 1:1. This phase ratio may be varied, based dependently on the amount of the alumina included in the zirconia electrolyte layers 131, 121. The phase ratio is determined by a known X-ray diffraction analysis, specifically based on comparison of X-ray diffraction peak intensities on monoclinic, tetragonal and/or cubic phases between samples of known values and specimens to be analyzed, detected on crystal face (400) for cubic phase and crystal faces (004) and (220) for tetragonal phase.

So long as this phase ratio falls in the above range of from 1:4 to 2:1 with inclusion of alumina in the zirconia used in the second oxygen-ion conductive solid electrolyte layer 121 of the oxygen-pumping cell 121 and with substantially no monolithic phase that causes a volume change of zirconia (due to phase transformation) leading to cracks of the solid electrolyte layer 121, a sensor having a laminate (1*a*) shows good durability and structural strength and does not malfunction in a thermal cycling environment.

Figure 6:
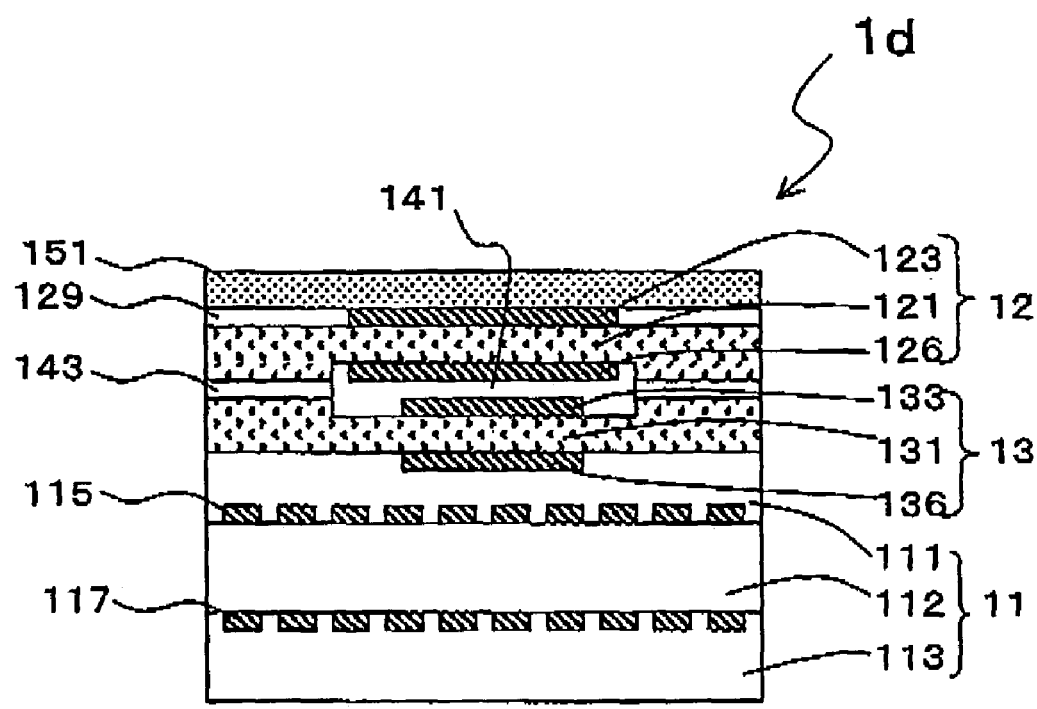
FIG. 6 is a schematic transverse sectional view of another gas sensor embodiment according to the present invention.

An ion-leakage preventing ceramic spacer 143 made mainly of alumina forms a diffusion space 141. The ion-leakage preventing spacer 143 is, as shown in FIG. 3, laminated and co-fired with the first oxygen-ion conductive solid electrolyte layer 131, the lead 134 of the oxygen-detecting cell 12 and the reduction-prevention insulative layer 138 interposed between the lead 134 and the first solid electrolyte layer 131. When the thickness of the ion-leakage preventing ceramic spacer 143 is decreased, as shown in FIG. 6, the thickness of the first and/or second solid electrolyte layers 131, 121 may be increased so as to ensure a minimum gas-diffusion space 141 between an oxygen-detecting electrode 133 of the oxygen-detecting cell 13 and an inner electrode 126 of the oxygen-pumping electrode 12.

The ion-leakage preventing ceramic spacer 143 has a notched portion near or at one of its distal ends so as to form the diffusion space 141 and to incorporate therein a gas diffusion passage 142 filled with a porous insulative alumina ceramic. The ion-leakage preventing ceramic spacer 143 is so shaped to prevent oxygen-ions of a second oxygen-ion conductive solid electrolyte layer 132 from leaking to the first oxygen-ion conductive solid electrolyte layer 121, in co-operation with the diffusion passage 142 filled with the porous insulative ceramic material.

Since the ion-leakage prevention spacer is made mainly of alumina, its high thermal conductivity is advantageous in minimizing a temperature difference between the first and second solid electrolyte layers 121, 131 and in transferring a heating energy from the heating resistor 115 to the second solid electrolyte layer 121. Without such an ion-leakage preventing ceramic spacer 143, when the oxygen-pumping cell 12 pumps oxygen from or into the diffusion space 141, the second oxygen-ion conductive layer 12 leaks or floods its oxygen-ions into the first oxygen-ion conductive layer 131, causing erroneous detection of electromotive force generated across the oxygen-detecting electrodes 133 and the oxygen-reference electrode 136 of the oxygen-detecting cell 13 and resulting in erroneous measurement of ionic current that flows across the oxygen-pumping cell 12. Therefore, this ion-leakage prevention ceramic spacer 143 is necessarily laminated directly or indirectly with the first oxygen-ion conductive solid electrolyte layer 131 to provide accurate detection or sensing of oxygen amount (or oxygen concentration) by the oxygen-detecting cell 13.

Notably, in order to further prevent erroneous measurement or other adverse effects of ion-leakage, at least one electrically conductive line running via through-holes penetrating the first and/or second oxygen-ion conductive solid electrolyte layers 131, 121 may be insulated from the first and/or oxygen-ion conductive solid electrolyte layers by a circumferential insulative layer 130 of alumina inside the through-holes, as shown in FIG. 2.

An electromotive force detected across the electrodes 133, 136 is related to the ratio between an oxygen-partial pressure of the gas atmosphere inside the gas diffusion space 141 and that of an oxygen-reference gas, according to the Nernst equation. Therefore, a voltage detected across the oxygen-detecting electrode 133 and the oxygen-reference electrode 136 is indicative of oxygen partial pressure inside the gas diffusion space 141.

A second oxygen-ion conductive solid electrolyte layer 121 is laminated and co-fired with the oxygen-ion leakage preventing ceramic spacer 143 that is laminated and co-fired with the first oxygen-ion conductive solid electrolyte layers 131 that is laminated and co-fired with the alumina substrate 11. The second oxygen-ion conductive solid electrolyte layer 121 is indirectly co-fired with the alumna substrate 11 through the first oxygen-ion conductive solid electrolyte layer 121 intervening therebetween.

A portion of the second-ion conductive solid electrolyte layer 121 constitutes the oxygen-pumping cell 12 with outer and inner electrodes 123, 126 formed on different respective faces of the second-ion conductive solid electrolyte layer 121. The second oxygen-ion conductive solid electrolyte layer 121 is of a rectangular shape with two through-holes; one is formed near a corner formed by its one distal end and longitudinal side end, while the other is formed close to a middle of the distal end. The through-hole formed near the corner is used for electrical connection for the lead 137 of the oxygen-detecting cell 131.

The lead 127 that is formed extendedly from an inner electrode 126 of the second-ion conductive solid electrolyte layer 121 and further extended along about a longitudinal center of an ion-leakage-prevention ceramic spacer 143, is electrically connected to the second outer pad 154 formed on a surface of the reinforcing insulative cover layer 152 via a through-hole penetrating the first and second reduction-preventing insulative layers 128, 129, the second solid electrolyte layer 121, and the reinforcing insulative ceramic cover 152, and is electrically connected with the lead 134 of the oxygen-detecting electrode 133 of the of the oxygen-detecting cell 13 as shown in FIGS. 2 and 3, so that the inner electrode 126 of the pumping electrode 12 and the oxygen-detecting electrode 133 of the oxygen-detecting cell 13 can be electrically charged with the same electric potential.

A first reduction-preventing insulative layer 128 is interposed between the lead 127 and the second oxygen-ion conductive solid electrolyte layer 121, for preventing so called "blackening" or rather reduction or deoxidization of zirconia contained in the second oxygen-ion layer 121 surrounding the lead 127.

A lead 124 is electrically connected to the third outer pad 153 formed on the surface of the reinforcing insulative ceramic layer 152, as understood by FIG. 3, via a through-hole penetrating the reinforcing insulative ceramic cover 152 and is also electrically connected to the outer electrode 123 of the oxygen-pumping cell 12. The lead 124 is formed and co-fired between the reinforcing insulative cover 152 and the second reduction-preventing insulative layer 129 that prevents blackening or rather reduction or deoxidization of zirconia contained in the second solid electrolyte layer 121 surrounding the lead 124. The lead 124 runs near along a longitudinal side of the second oxygen-ion conductive solid electrolyte layer 121 and from the outer electrode 123 formed near a distal end portion of the second solid electrolyte layer 112 to the other distal end portion where the two through-holes are formed through the oxygen-ion conductive solid electrolyte layer 121.

The inner and outer electrodes 126, 123 of the oxygen-pumping cell 12 are positioned to correspond to the position of the oxygen-detecting electrode 133 of the oxygen-detecting cell 13, which in turn is positioned apart and spaced by the gas-diffusion space 141 from the inner electrode 126. The second oxygen-ion conductive solid electrolyte layer 121 interfaces with the inner electrode 126 of the oxygen-ion pumping cell 12, the ion leakage preventing ceramic spacer 143 and the first reduction-preventing insulative layer 128. The oxygen-ion conductive-solid electrolyte layer 121 also interfaces with the outer electrode 123 of the oxygen-ion pumping cell 12 and the second reduction-preventing insulative layer 129.

The second reduction-preventing insulative layer 129 has a large hole of a rectangular shape at its distal end portion, in which hole the outer electrode 123 is formed on the oxygen-ion conductive solid electrolyte layer 121.

A gas diffusion space 141 is formed between an inner electrode 126 of the oxygen-pumping cell 12 and the oxygen-detecting electrode 133 of the oxygen-detecting cell and formed by the oxygen-ion leakage prevention spacer 143 and a gas-diffusion passage 142 filled with a porous alumina ceramic. The porous alumina ceramic renders a diffusion resistance against gas molecules entering the gas diffusion space 141, and prevents oxygen ion leakage across the two cells 12, 13.

The gas-diffusion passage 142 is formed between ends of the first and second oxygen-ion conductive solid electrolyte layers 131,121. The gas-diffusion passage 142 is filled with a porous insulative ceramic material such as porous alumina having a diffusion resistance that physically limits the amount of molecules of gaseous components entering or rather diffusing into the gas diffusion space 141. Since the gaseous molecules including oxygen are limited by the diffusion resistance of the gas-diffusion passage 142, an amount of oxygen inside the gas-diffusion space 141 can be controlled to a constant target value by pumping oxygen in or out of the gas-diffusion space 141. Feedback control is effected through a control circuit by comparing an oxygen partial pressure value detected inside the gas-diffusion space 142 with the target value and then electrically ordering the oxygen-pumping cell to pump out oxygen (if the oxygen is abundant inside the diffusion space) or to pump in oxygen (if the oxygen is scarce therein) with proper polarity of voltage applied across the inner and outer electrodes 123, 126 of the oxygen-pumping cell 12 so long as there is a difference between the two values. In this manner, oxygen is ionized to flow through the oxygen-ion conductive layer 121 sandwiched by the electrodes 121, 123 of the oxygen-pumping cell 12. The ionized oxygen flowing across the electrodes 121, 123 can be electrically measured as an ionic current of the oxygen-pumping cell. This ionic current can be used as an indicator of a state of oxygen amount or partial oxygen pressure of the ambient gas such as an exhaust gas of an internal combustion engine, covering a wide range of air fuel ratio from fuel-lean to fuel-rich, when an entering speed and an out-going speed of the oxygen inside the gas-diffusion space 141 are well balanced by design.

Figure 4:
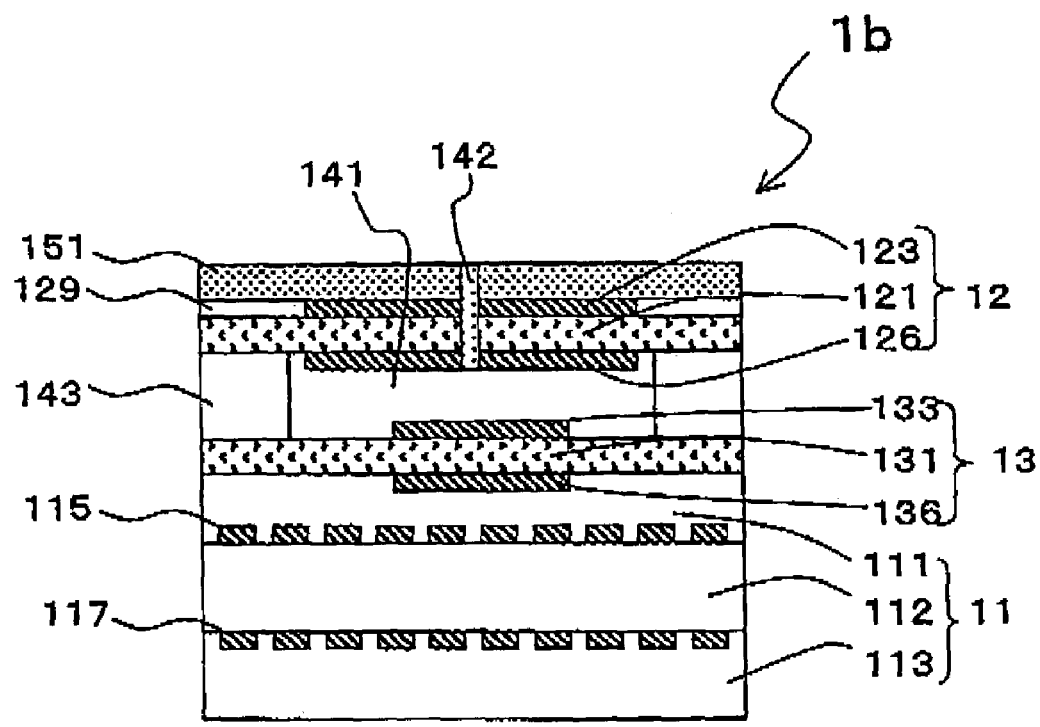
FIG. 4 is a schematic transverse sectional view of another gas sensor embodiment according to an aspect of the present invention.
Figure 5:
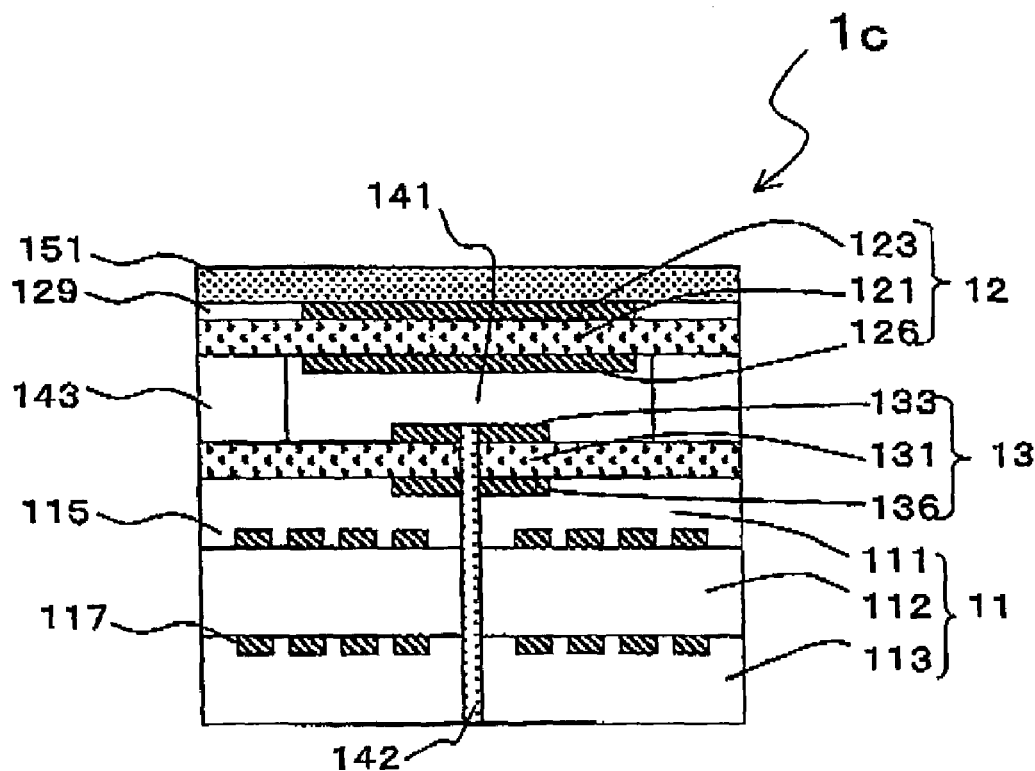
FIG. 5 is a schematic transverse sectional view of another gas sensor embodiment according to the present invention.
Figure 7:
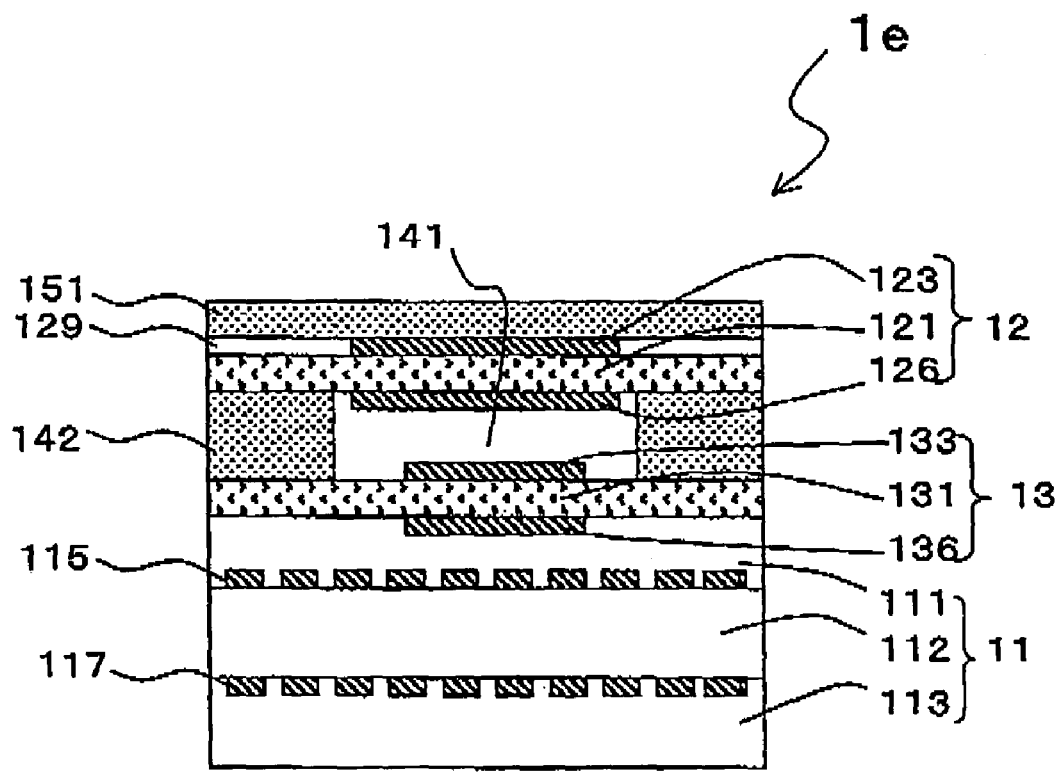
FIG. 7 is a schematic transverse sectional view of another gas sensor embodiment according to the present invention.

As shown in FIG. 7, two gas-diffusion passages 142 each with a diffusion resistance may be formed between sides of the oxygen-ion conductive layers 131 and 132. Such a gas-diffusion passage 142 may be formed alternatively as shown in FIG. 4, penetrating an oxygen-pumping cell 12 and a porous protective cover 151 covering an outer electrode of the pumping cell 12 or further alternatively as shown in FIG.

5, penetrating an oxygen-detecting cell 13 and an alumina substrate 11 in which a heating resistor 115 and/or an ionic migration prevention preventing electrode 117 are embedded. Among these gas-diffusion passage choices, plural gas-diffusion passages formed as shown in FIG. 7 become most advantageous. Namely, adjustment of diffusion resistance becomes easy because of the plural passages each filled with a porous insulative material.

Referring back to FIG. 3, the reduction-preventing insulative layer 138 mainly made of alumina provided between the lead 134 of the oxygen-detecting cell 13 and the solid electrolyte layer 131, is co-fired therewith. Although the lead 134 thereof is not so seriously reduced or deoxidized, accurate detection of electromotive force generated across the detecting electrode 133 and the reference electrode 136 of the oxygen-detecting cell 13 is effectively improved, compared to a sensor laminate without the insulative layer 138.

Two other reduction-preventing insulative layers 128, 129 made mainly of alumina are importantly provided and cofired between the second oxygen-ion conductive solid electrolyte layer 121 and the leads 124, 128 respectively. These reduction-preventing insulative layers 128, 129 protect zirconia of the oxygen-ion conductive solid electrolyte layer 121 surrounding the leads from blackening (meaning deoxidization or reduction). This "blackening" phenomenon liable to occur without the insulative layers 128, 129 is caused by a voltage applied across the leads 124 of an outer electrode 123 and an inner electrode 126 of the oxygen-pumping cell 12 for pumping oxygen into or out of the gas-diffusion space 141. Specifically, the "blackening" occurs around the electrode 127 in the fuel-lean state and it occurs around the electrode 124 in the fuel-lean state, depending on the applied voltage polarity subjected thereto.

A reinforcing insulative cover 152 mainly made of alumina is co-fired on the second oxygen ion-conductive layer 121 and the lead 124 of the oxygen-pumping cell 12 so as to protect them electrically and to mechanically increase the overall strength of the laminate (1a).

A porous insulative cover 151 is formed on the outer electrode 123 entirely covering it. A preferable material for this cover 151 is, for instance, porous alumina or porous spinel. The porous insulative cover 151 prevents the outer electrode 123 of the pumping cell 12 from contaminants such as water, dirt including Si, Pb, P, etc. contained in ambient exhaust gas from an internal combustion engine.

Dimensional and functional optimization is inevitable in designing the laminate (1a) and selecting materials for the laminated components thereof. With respect to the overall dimension of the laminate (1a) for a gas sensor such as a full range air-fuel ratio sensor for use in controlling an automobile combustion engine, the longitudinal length, width, and thickness of the laminate should be optimized within 30–60 mm, 3–6 mm, and 1–3 mm, respectively. If the length is less than 30 mm, the area where the outer terminal pads 153, 154, 155 becomes too hot and the electrical insulation between the pads is lost under a practical high temperature environment.

Specifically, the thickness of the first oxygen-ion conductive solid electrolyte layer 131 that is closely laminated on the alumina substrate 11 embedding the heating resistor 115 is optimized in the range of 10–200, preferably 20–100 and more preferably 30–70 in micrometers. If it is less than 10 micrometers, sufficient electromotive force or voltage is not generated across the oxygen-detecting cell 13. If it is more than 200 micrometers, heating efficiency for the oxygen-pumping cell 12 by the heating resistor is greatly affected.

With respect to the thickness of the second oxygen-ion conductive solid electrolyte layer 121, the minimum thickness is increased to 30 micrometers, compared to that of the first solid electrolyte layer 131. This is because a portion of the solid electrolyte layer 121 required for an oxygen-pumping function of the oxygen-pumping cell 12 is suspended over the gas diffusion space 141 and not supported by a sturdy substrate, except by the outer electrode 123 and the porous insulative cover 151 which are not sturdy, compared to the alumina substrate 11 by which the first solid electrolyte layer 131 is entirely supported. However the maximum thickness of the second solid electrolyte layer 121 may not exceed 400 micrometers, primarily because the oxygen-pumping capability of the oxygen-pumping cell 12 is greatly affected due to limitation of allowable area for its inner and outer electrodes, which area is limited by the overall dimension of the laminate (1a) acceptable in a gas sensor housing as mentioned above. In addition, activation of the oxygen-pumping cell 12 is unimproved, even if alumina grains are added in the first and second solid electrolyte layer 131, 121 due to a volume increase of the suspended portion of the second solid electrolyte layer 121 for the oxygen-pumping cell 12 to be heated.

Notably, the suspended portion of the second solid electrolyte 121 is not sharply heated due to the diffusion gas space 141 blocking direct thermal transfer of heat generated by the heating resistor 115. This is advantageous for the gas sensor with the co-fired laminate (1a), since the oxygen-pumping cell 12 is protected or buffered from a thermal shock rendered by the heating resistor 115.

The thickness of the electrodes of the sensor cells 12, 13, is preferably in the range of about 3 to 30 micrometer (μm), or more preferably 10–25 μm. The area of the electrode 126 of the oxygen-pumping cell is preferably in the range of about 1–20 mm$^2$, or more preferably 6–10 mm$^2$. The area of the electrode 133 of the oxygen-detecting cell 13 is preferably 15–80% of that of the electrode 126 of the oxygen-pumping cell 12.

Inclusion of alumina grains into a solid electrolyte layer formed of partially stabilized zirconia suppress not only phase transformation but also grain growth of zirconia effectively, depending on the amount and average grain size of the alumina grains.

Suppression of the phase transformation and grain growth of zirconia becomes more effective when the included alumina grains are in an amount of 10–80% by weight and with an average grain size of less than 1 μm. Notably, since the alumina grains are not ion-conductive, purified alumina containing substantially no contaminant or less than 0.01% by weight of contaminant is most preferably recommended for a green (unfired) layer for the oxygen-ion conductive solid electrolyte layer 121 constituting the oxygen-pumping cell 12. The silica content especially should be substantially zero, because it damages the oxygen ion conductivity of the co-fired zirconia solid electrolyte layers 121, 131.

The average grain size of alumina powder to be contained in the green (unfired) oxygen-ion conductive solid electrolyte layers 121, 131 is preferably in the range of 0.1–0.5 micrometers. The average grain size of zirconia powder to be contained in a green layer for the oxygen-ion conductive layers 121, 131 is preferably in the range of 0.2–1.2 micrometers. The use of a co-precipitated zirconia powder containing 3–7 mol % yttria serving as a stabilizer is recommended.

When the solid electrolytic layer after co-firing contains alumina having an average grain size as mentioned above, the average grain size of YSZ (yttria stabilized zirconia)

after co-firing can be restrained to less than 2.5 μm. Since such YSZ containing alumina is used in the sensor laminate (1*a*), the phase transformation caused by a temperature rise and a temperature drop during a cold-hot thermal cycle in an actual environment in which the sensor laminate (1*a*) is used as a gas sensor is restrained very effectively. This is probably because a stress caused by the phase transformation is readily dispersed or absorbed by the fine alumina grains abundantly existing at zirconia grain boundaries such that the occurrence of cracks is prevented.

In production of the laminate (1*a*) that does not have an ionic migration-preventing electrode 117, highly purified alumina powder with contaminants of less than 1% by weight or substantially no contaminants (preferably of less than 0.1% by weight or most preferably less than 0.01% by weight) is used for preparing green layers for the first and second alumina layers 111, 112 surrounding the heating resistor 115 and for the first and second oxygen-ion conductive solid electrolyte layers 113, 121. In preparing these green layers 113, 121 and/or other green layers 128, 129, 138, 143, 152 for co-firing the laminate (1*a*), a known method such as a doctor blade method and a sheet-rolling method may be applied. A screen-printing method may be used for printing unfired electrodes 133, 136, 123, 126 and/or unfired leads thereof 134, 137, 124, 127 onto the green first and second solid electrolyte layers 131, 121 and/or other green layers 127, 129, 143, for printing unfired heating resistor 115 and leads thereof 116 onto unfired second alumina layer 112, for printing unfired outer terminal pads 157(+), 156(−) onto green second alumina layer 112 (or 113), and for printing unfired first, second and third outer terminal pads 155, 154, 153 onto green reinforcing insulative cover 152 layer. The screen-printing method is also applicable in forming the porous protective cover 151 and the porous material filled in the gas-diffusion passage 142. Notably, a material for the porous protective cover 151 and the porous material to be filled in the gas-diffusion passage 142 are made by mixing 30–70% by volume of alumina powder and 70–30% by volume of carbon powder and co-firing with other laminated components.

In production of the laminate (1*a*) that has a migration-preventing electrode 117 embedded in the alumina substrate 11, similar methods as described above are applicable, except that metal oxides such as MgO, CaO, BaO, $SiO_2$ may be used as inorganic binders in green alumina substrate 11 comprising green first, second and third alumina layers 111, 112, 113 and that an unfired migration-preventing electrode 117 is printed on the unfired third alumina layer 113.

After laminating these unfired components containing necessary organic binders to form an unfired laminate (1*a*), the unfired laminate (1*a*) is simultaneously sintered (i.e., co-fired) under an optimized firing schedule, for instance, of gradually elevating the temperature by 10 degrees centigrade per hour up to 420 degrees centigrade and holding for two hours at that temperature, then elevating by 100 degrees centigrade per hour up to 1100 degrees centigrade and further elevating by 60 degrees centigrade per hour up to 1520 degrees centigrade at which temperature holding for one hour, and then cooling so as to attain a co-fired gas sensor laminate (1*a*) that operates as a full range air/fuel ratio sensor (or so called UEGO: universal exhaust gas oxygen sensor).

In operation of the sensor laminate (1*a*) thus attained, firstly a dc voltage of about 13 V is applied across the terminal pads 156(−), 157(+) so as to heat and activate the sensor cells 12, 13. Then a negligibly little constant current of about 10 microampere is flowed across the oxygen-detecting electrode 133 and the reference electrode 136 of the oxygen detecting cell 12 through an resistor so that the reference electrode 136 maintains a constant oxygen partial pressure of about 2 atm for use as a reference. Excess oxygen in the reference electrode drains through the lead 137 thereof that is porous. The oxygen-detecting electrode 133 now determines an oxygen partial pressure inside the gas diffusion space 141 because the reference electrode 136 holds a constant referable oxygen partial pressure. At this moment, when the oxygen partial pressure inside the gas diffusion space 141 is not a predetermined value (corresponding to, e.g., stoichiometric air fuel ratio λ), a controller electrically orders the oxygen-pumping cell 12 to pump oxygen in or out of the gas diffusion space 141 until the oxygen-detecting cell 13 detects the predetermined value (of about 450 mV corresponding to λ). Therefore, as is well known, an ionic pumping current flowing across the electrodes 123, 126 of the oxygen-pumping cell 12 becomes indicating an extent of oxygen amount away from the predetermined value (corresponding to λ) and referring to a burning state of the fuel in an internal combustion engine. Based on this ionic current, the internal combustion engine can control an air-fuel ratio from fuel-lean to rich and/or a burning condition of the fuel in the engine. Additional functional details of the UEGO are described in "The Fundamentals of Automotive Engine Control Sensors, authored by Kanemitsu Nishio, published by Fontis Media (Switzerland, 2001).

The gas sensor having the sensor laminate (1*a*) according to the invention survives a 500-hour thermal cycling durability test conducted on an engine dyno fixture in which the temperature reversibly varies between 350 to 930 degrees centigrade in a hour under A/F ratio shifting of 12 to 30.

The present invention is not limited to the above-described embodiments. Numerous modifications and variations in the present invention are possible according to purpose or application without departing from the scope of the invention.

This application is based on Japanese Patent Application No. 2002-320479 filed Nov. 1, 2002, the disclosure of which is incorporated herein by reference in its entirety.

What is claimed is:

1. A gas sensor (1*a*) having a laminate comprising:
    an alumina substrate (11) having a heating resistor (115) embedded in the alumina substrate (11);
    a first oxygen-ion conductive solid electrolyte layer (131) containing zirconia and alumina and partly constituting an oxygen-detecting cell (13) and said first solid electrolyte layer (131) being laminated with said alumina substrate (11);
    a second oxygen-ion conductive solid electrolyte layer (121) containing zirconia and alumina and partly constituting an oxygen-pumping cell (12);
    an ion-leakage preventing ceramic spacer (143) for preventing oxygen-ions from leaking from the second oxygen-ion conductive solid electrolyte layer (121) to the first oxygen-ion conductive solid electrolyte layer (131), said spacer (143) being laminated between said first and second oxygen-ion conductive solid electrolyte layers (131, 121); and
    a gas-diffusion space (141) formed between an electrode (133) of the oxygen-detecting cell (13) and an electrode (126) of the oxygen-pumping cell (12);
    wherein the first and second oxygen-ion conductive solid electrolyte layers contain alumina grains, and wherein the second oxygen-ion conductive solid electrolyte layer (121) contains alumina in an amount less than that of the first oxygen-ion conductive solid electrolyte layer (131).

2. The gas sensor as claimed in claim 1, wherein the laminate is a co-fired laminate.

3. The gas sensor as claimed in claim 1, further comprising an ionic migration-preventing electrode (117) for preventing the heating resistor (115) from deterioration or electrical disconnection, wherein an electric potential of said ionic migration-preventing electrode (117) is equal to or lower than the lowest electric potential of any part of the heating resistor (115).

4. The gas sensor as claimed in claim 3, wherein said ionic migration-preventing electrode (117) is formed between an outer surface of the alumina substrate (11) and the heating resistor (115).

5. The gas sensor as claimed in claim 4, wherein the first and second oxygen-ion conductive solid electrolyte layers (131, 121) contain 10–80% by weight of alumina, respectively, and an average grain size of alumina contained in the first and/or second oxygen-ion conductive solid electrolyte layers (131, 121) is less than 1 micrometer.

6. The gas sensor as claimed in claim 4, wherein a phase of the zirconia contained in the first and/or second oxygen-ion conductive solid electrolyte layer consists essentially of a cubic phase and a tetragonal phase.

7. The gas sensor as claimed in claim 4, wherein the second oxygen-ion conductive solid electrolyte layer (121) contains alumina in an amount that is at least 5% by weight less than that of the first oxygen-ion conductive electrolyte layer (131).

8. The gas sensor as claimed in claim 3, wherein said ionic migration-preventing electrode (117) is connected to a portion of leads (116) of negative polarity, said portion being lower than the heating resistor (115) in electric potential.

9. The gas sensor as claimed in claim 3, wherein the first and second oxygen-ion conductive solid electrolyte layers (131, 121) contain 10–80% by weight of alumina, respectively, and an average grain size of alumina contained in the first and/or second oxygen-ion conductive solid electrolyte layers (131, 121) is less than 1 micrometer.

10. The gas sensor as claimed in claim 3, wherein a phase of the zirconia contained in the first and/or second oxygen-ion conductive solid electrolyte layer substantially consists of a cubic phase and a tetragonal phase.

11. The gas sensor as claimed in claim 3, wherein the second oxygen-ion conductive solid electrolyte layer (121) contains alumina in an amount that is at least 5% by weight less than that of the first oxygen-ion conductive electrolyte layer (131).

12. The gas sensor as claimed in claim 1, wherein the second oxygen-ion conductive solid electrolyte layer (121) constituting the oxygen-pumping cell (12) contains 10–80% by weight of alumina.

13. The gas sensor as claimed in claim 1, wherein the first oxygen-ion conductive solid electrolyte layer (131) constituting the oxygen-concentration cell (13) contains 10–80% by weight of alumina.

14. The gas sensor as claimed in claim 1,
wherein the first and second oxygen-ion conductive solid electrolyte layers (131, 121) contain 10–80% by weight of alumina, respectively, and an average grain size of alumina contained in the first and/or second oxygen-ion conductive solid electrolyte layers (131, 121) is less than 1 micrometer.

15. The gas sensor as claimed in claim 14, wherein a phase of the zirconia contained in the first and/or second oxygen-ion conductive solid electrolyte layer substantially consists of a tetragonal phase and/or cubic phase.

16. The gas sensor as claimed in claim 14, wherein the second oxygen-ion conductive solid electrolyte layer (121) contains alumina in an amount that is at least 5% by weight less than that of the first oxygen-ion conductive electrolyte layer (131).

17. The gas sensor as claimed in claim 14,
wherein the second oxygen-ion conductive solid electrolyte layer 121 constituting the oxygen-pumping cell (12) contains 60 to 90% by weight of zirconia and 10–40% by weight of alumina, and
wherein the second oxygen-ion conductive solid electrolyte layer (121) constituting the oxygen-pumping cell (12) contains alumina in an amount that is 10 to 50% by weight less than that of the first oxygen-ion conductive electrolyte layer (131) constituting the oxygen-detecting cell (13).

18. The gas sensor as claimed in claim 14, further comprising an electrode (136) and a lead (137),
wherein the electrode (136) constituting the oxygen-concentration detecting cell (13) and facing the alumina substrate (11) is a reference electrode capable of storing oxygen therein and communicating with an atmosphere outside the sensor (1a) through a lead (137) connected to the electrodes (136), said lead (137) serving as a channel (16) for draining oxygen.

19. The gas sensor as claimed in claim 14, wherein an area of the said electrode (133) of the oxygen-detecting cell (13) is 15 to 80% that of the electrode (126) of the oxygen-pumping cell (12).

20. The gas sensor as claimed in claim 1,
wherein the second oxygen-ion conductive solid electrolyte layer (121) constituting the oxygen-pumping cell (12) contains 60 to 90% by weight of zirconia and 10–40% by weight of alumina,
wherein the first oxygen-ion conductive solid electrolyte layer (131) constituting the oxygen-detecting cell (13) contains 40 to 80% by weight of zirconia and 20–60% by weight of alumina, and
wherein the second oxygen-ion conductive solid electrolyte layer (121) constituting the oxygen-pumping cell (12) contains alumina in an amount that is 10 to 50% by weight less than that of the first oxygen-ion conductive electrolyte layer (131) constituting the oxygen-detecting cell (13).

21. The gas sensor as claimed in claim 1, further comprising an electrode (136) and a lead (137),
wherein the electrode (136) constituting the oxygen-concentration detecting cell (13) and facing the alumina substrate (11) is a reference electrode capable of storing oxygen therein and communicating with an atmosphere outside the sensor (1a) through a lead (137) connected to the electrodes (136), said lead (137) serving as a channel (16) for draining oxygen.

22. The gas sensor as claimed in claim 1, further comprising a reduction-preventing insulative layer (128) for preventing deoxidation of the second oxygen-ion conductive layer (121) around the lead (127) of the oxygen-pumping cell (12), said reduction-preventing insulative layer (128) being provided between a lead (127) of the oxygen-pumping cell (12) and the oxygen-ion conductive solid electrolyte layer (121).

23. The gas sensor as claimed in claim 1, wherein said alumina substrate contains at least 99% by weight of alumina.

24. The gas sensor as darned in claim 1, further comprising a reinforcing insulative cover (152) for reinforcing the second oxygen ion-conductive layer (121) and covering the lead (124) of the oxygen pumping cell (12).

25. The gas sensor as claimed in claim 1, wherein a distance between the electrodes (126, 133) defining the gas diffusion space (141) is 20 to 80 micrometers.

26. The gas sensor as claimed in claim 1, wherein a thickness of the oxygen-ion conductive solid electrolyte layer (131) constituting the oxygen-detecting cell (13) is 10–200 micrometers, said gas sensor further comprising an electrode (136) located between the oxygen-ion conductive solid electrolyte layer (131) and the alumina substrate (11) and having a thickness of 1–20 micrometers.

27. The gas sensor as claimed in claim 1, further comprising a gas-diffusion passage (142) through which the measurement gas enters the gas diffusion space (141), said gas-diffusion passage (142) being formed through the ion-transfer prevention spacer (143).

28. The gas sensor as claimed in claim 1, wherein said ion-leakage preventing ceramic spacer (143) is made mainly of alumina.

29. The gas sensor as claimed in claim 1, wherein a thickness of the second oxygen-ion conductive solid electrolyte layer (121) is 30–400 micrometers.

30. The gas sensor as claimed in claim 1, wherein a phase formed in the zirconia contained in the first and/or second oxygen-ion conductive solid electrolyte layers consists essentially of a cubic phase and tetragonal phase, with a phase ratio of cubic phase to tetragonal phase being from 1:4 to 2:1.

31. The gas sensor as claimed in claim 1, a content of the alumina contained in the alumina substrate (11) is at least 70% by weight.

32. A gas sensor (1a) having a laminate comprising:
an alumina substrate (11) having a heating resistor (115) embedded in the alumina substrate (11);
a first oxygen-ion conductive solid electrolyte layer (131) containing zirconia and alumina and partly constituting an oxygen-detecting cell (13) and said first solid electrolyte layer (131) being laminated with said alumina substrate (11);
a second oxygen-ion conductive solid electrolyte layer (121) containing zirconia and alumina and partly constituting an oxygen-pumping cell (12);
an ion-leakage preventing ceramic spacer (143) for preventing oxygen-ions from leaking from the second oxygen-ion conductive solid electrolyte layer (121) to the first oxygen-ion conductive solid electrolyte layer (131), said spacer (143) being laminated between said first and second oxygen-ion conductive solid electrolyte layers (131, 121); and
a gas-diffusion space (141) formed between an electrode (133) of the oxygen-detecting cell (13) and an electrode (126) of the oxygen-pumping cell (12),
wherein the first and second oxygen-ion conductive solid electrolyte layers contain alumina grains;
wherein the laminate is a co-fired laminate;
wherein the first and second oxygen-ion conductive solid electrolyte layers (131, 121) contain 10–80% by weight of alumina, respectively, and an average grain size of alumina contained in the first and/or second oxygen-ion conductive solid electrolyte layers (131, 121) is less than 1 micrometer; and wherein the second oxygen-ion conductive solid electrolyte layer (121) contains alumina in an amount less than that of the first oxygen-ion conductive electrolyte layer (131).

33. The gas sensor as claimed in claim 32, wherein the second oxygen-ion conductive solid electrolyte layer (121) contains alumina in an amount that is at least 5% by weight less than that of the first oxygen-ion conductive electrolyte layer (131).

34. The gas sensor as claimed in claim 32,
wherein the second oxygen-ion conductive solid electrolyte layer 121 constituting the oxygen-pumping cell (12) contains 60 to 90% by weight of zirconia and 10–40% by weight of alumina, and
wherein the second oxygen-ion conductive solid electrolyte layer (121) constituting the oxygen-pumping cell (12) contains alumina in an amount that is 10 to 50% by weight less than that of the first oxygen-ion conductive electrolyte layer (131) constituting the oxygen-detecting cell (13).

35. The gas sensor as claimed in claim 32, further comprising an electrode (136) and a lead (137),
wherein the electrode (136) constituting the oxygen-concentration detecting cell (13) and facing the alumina substrate (11) is a reference electrode capable of storing oxygen therein and communicating with an atmosphere outside the sensor (1a) through a lead (137) connected to the electrodes (136), said lead (137) serving as a channel (16) for draining oxygen.

36. The gas sensor as claimed in claim 32, further comprising a reduction-preventing insulative layer (128) for preventing deoxidation of the second oxygen-ion conductive layer (121) around the lead (127) of the oxygen-pumping cell (12), said reduction-preventing insulative layer (128) being provided between a lead (127) of the oxygen-pumping cell (12) and the oxygen-ion conductive solid electrolyte layer (121).

37. A gas sensor (1a) having a laminate comprising:
an alumina substrate (11) having a heating resistor (115) embedded in the alumina substrate (11);
a first oxygen-ion conductive solid electrolyte layer (131) containing zirconia and alumina and partly constituting an oxygen-detecting cell (13) and said first solid electrolyte layer (131) being laminated with said alumina substrate (11);
a second oxygen-ion conductive solid electrolyte layer (121) containing zirconia and alumina and partly constituting an oxygen-pumping cell (12);
an ion-leakage preventing ceramic spacer (143) for preventing oxygen-ions from leaking from the second oxygen-ion conductive solid electrolyte layer (121) to the first oxygen-ion conductive solid electrolyte layer (131), said spacer (143) being laminated between said first and second oxygen-ion conductive solid electrolyte layers (131, 121); and
a gas-diffusion space (141) formed between an electrode (133) of the oxygen-detecting cell (13) and an electrode (126) of the oxygen-pumping cell (12),
wherein the first and second oxygen-ion conductive solid electrolyte layers contain alumina grains,
wherein the laminate is a co-fired laminate;
wherein the second oxygen-ion conductive solid electrolyte layer (121) constituting the oxygen-pumping cell (12) contains 60 to 90% by weight of zirconia and 10–40% by weight of alumina;

wherein the first oxygen-ion conductive solid electrolyte layer (131) constituting the oxygen-detecting cell (13) contains 40 to 80% by weight of zirconia and 20–60% by weight of alumina; and wherein the second oxygen-ion conductive solid electrolyte layer (121) constituting the oxygen-pumping cell (12) contains alumina in an amount that is 10 to 50% by weight less than that of the first oxygen-ion conductive electrolyte layer (131) constituting the oxygen-detecting cell (13).

38. The gas sensor as claimed in claim 37, further comprising an electrode (136) and a lead (137)

wherein the electrode (136) constituting the oxygen-concentration detecting cell (13) and facing the alumina substrate (11) is a reference electrode capable of storing oxygen therein and communicating with an atmosphere outside the sensor (1a) through a lead (137) connected to the electrodes (136), said lead (137) serving as a channel (16) for draining oxygen.

39. The gas sensor as claimed in claim 37, further comprising a reduction-preventing insulative layer (128) for preventing deoxidation of the second oxygen-ion conductive layer (121) around the lead (127) of the oxygen-pumping cell (12), said reduction-preventing insulative layer (128) being provided between a lead (127) of the oxygen-pumping cell (12) and the oxygen-ion conductive solid electrolyte layer (121).

40. A gas sensor (1a) having a laminate comprising:

an alumina substrate (11) having a heating resistor (115) embedded in the alumina substrate (11);

a first oxygen-ion conductive solid electrolyte layer (131) containing zirconia and alumina and partly constituting an oxygen-detecting cell (13) and said first solid electrolyte layer (131) being laminated with said alumina substrate (11);

a second oxygen-ion conductive solid electrolyte layer (121) containing zirconia and alumina and partly constituting an oxygen-pumping cell (12);

an ion-leakage preventing ceramic spacer (143) for preventing oxygen-ions from leaking from the second oxygen-ion conductive solid electrolyte layer (121) to the first oxygen-ion conductive solid electrolyte layer (131), said spacer (143) being laminated between said first and second oxygen-ion conductive solid electrolyte layers (131, 121); and a gas-diffusion space (141) formed between an electrode (133) of the oxygen-detecting cell (13) and an electrode (126) of the oxygen-pumping cell (12), wherein the first and second oxygen-ion conductive solid electrolyte layers contain alumina grains;

wherein the laminate is a co-fired laminate;

further comprising an ionic migration-preventing electrode (117) for preventing the heating resistor (115) from deterioration or electrical disconnection, wherein an electric potential of said ionic migration-preventing electrode (117) is equal to or lower than the lowest electric potential of any part of the heating resistor (115); and wherein the second oxygen-ion conductive solid electrolyte layer (121) contains alumina in an amount less than that of the first oxygen-ion conductive electrolyte layer (131).

41. The gas sensor as claimed in claim 40, wherein the second oxygen-ion conductive solid electrolyte layer (121) constituting the oxygen-pumping cell (12) contains 10–80% by weight of alumina.

42. The gas sensor as claimed in claim 40, wherein the first oxygen-ion conductive solid electrolyte layer (131) constituting the oxygen-concentration cell (13) contains 10–80% by weight of alumina.

43. The gas sensor as claimed in claim 40, further comprising a reduction-preventing insulative layer (128) for preventing deoxidation of the second oxygen-ion conductive layer (121) around the lead (127) of the oxygen-pumping cell (12), said reduction-preventing insulative layer (128) being provided between a lead (127) of the oxygen-pumping cell (12) and the oxygen-ion conductive solid electrolyte layer (121).

44. The gas sensor as claimed in claim 40, wherein the second oxygen-ion conductive solid electrolyte layer (121) contains alumina in an amount that is at least 5% by weight less than that of the first oxygen-ion conductive electrolyte layer (131).

45. The gas sensor as claimed in claim 40, wherein said ionic migration-preventing electrode (117) is formed between an outer surface of the alumina substrate (11) and the heating resistor (115).

46. The gas sensor as claimed in claim 45, wherein the second oxygen-ion conductive solid electrolyte layer (121) constituting the oxygen-pumping cell (12) contains 10–80% by weight of alumina.

47. The gas sensor as claimed in claim 45, wherein the first oxygen-ion conductive solid electrolyte layer (131) constituting the oxygen-concentration cell (13) contains 10–80% by weight of alumina.

48. The gas sensor as claimed in claim 45, further comprising a reduction-preventing insulative layer (128) for preventing deoxidation of the second oxygen-ion conductive layer (121) around the lead (127) of the oxygen-pumping cell (12), said reduction-preventing insulative layer (128) being provided between a lead (127) of the oxygen-pumping cell (12) and the oxygen-ion conductive solid electrolyte layer (121).

49. The gas sensor as claimed in claim 45, wherein the second oxygen-ion conductive solid electrolyte layer (121) contains alumina in an amount that is at least 5% by weight less than that of the first oxygen-ion conductive electrolyte layer (131).

* * * * *